US008796449B2

(12) United States Patent
Kallenbach

(10) Patent No.: US 8,796,449 B2
(45) Date of Patent: Aug. 5, 2014

(54) S-TRIAZINE COMPOUNDS, PHARMACEUTICAL COMPOSITIONS AND METHODS OF USING THE SAME

(75) Inventor: Neville Robert Kallenbach, Philadelphia, PA (US)

(73) Assignee: New York University, New York, NY (US)

(*) Notice: Subject to any disclaimer, the term of this patent is extended or adjusted under 35 U.S.C. 154(b) by 413 days.

(21) Appl. No.: 13/049,988

(22) Filed: Mar. 17, 2011

(65) Prior Publication Data

US 2011/0230489 A1 Sep. 22, 2011

Related U.S. Application Data

(60) Provisional application No. 61/314,991, filed on Mar. 17, 2010.

(51) Int. Cl.

*C07D 251/70* (2006.01)
*C07D 403/12* (2006.01)
*C07D 403/14* (2006.01)
*A61K 31/53* (2006.01)
*A61P 31/04* (2006.01)

(52) U.S. Cl.

CPC ............ *C07D 251/70* (2013.01); *C07D 403/12* (2013.01); *C07D 403/14* (2013.01); *A61K 31/53* (2013.01)

USPC ............ 544/197; 544/198; 544/209; 514/245

(58) Field of Classification Search

CPC ..... C07D 251/70; C07D 403/14; A61K 31/53

USPC ........................... 544/197, 198, 209; 514/245

See application file for complete search history.

(56) References Cited

U.S. PATENT DOCUMENTS

| | | | | |
|---|---|---|---|---|
| 4,654,384 | A * | 3/1987 | Ramanathan et al. | 534/604 |
| 6,117,996 | A * | 9/2000 | Lowe et al. | 544/216 |
| 6,887,873 | B2 * | 5/2005 | Mailliet et al. | 514/245 |
| 7,585,361 | B2 * | 9/2009 | Yoneda et al. | 106/31.47 |
| 2009/0151599 | A1 * | 6/2009 | Fujii et al. | 106/31.47 |

OTHER PUBLICATIONS

Wolff Manfred E. "Burger's Medicinal Chemistry, 5ed, Part 1", John Wiley & Sons, 1995, pp. 975-977.*

Banker, G.S. et al, "Modern Pharmaceutices, 3ed.", Marcel Dekker, New York. 1996, pp. 451 and 596.*

West, Anthony R., Solid State Chemistry and its Applications, Wiley, New York, 1988, pp. 358 & 365.*

Vippagunta et al., Advanced Drug Delivery Reviews 48: 3-26, 2001.*

Hulikal, V. Deuterium Labeled Compounds in Drug Discovery Process, 2010. Abstract provided-see also www.hwb.gov.in/htmldocs/nahwd201 O/L15.pdf.*

Pimlott SL., Nucl. Med. Commun. 26(3): 183-188, 2005 (PubMed Abstract provided).*

Snyder et al., J. Med. Liban 48(4): 208-214, 2000. PubMed Abstract.*

Cecil Textbook of Medicine, edited by Bennet, J.C., and Plum F., 20th edition,vol. 1, 1004-101 O, 1996.*

Freshney et al.,Culture of Animal Cells, A Manual of Basic Technique, Alan R. Liss, Inc., 1983, New York, p. 4.*

Dermer et al., Bio/Technology, 1994, 12:320.*

Turner et al., Current Pharmaceutical Design. 2, 209-224, 1996.*

Sugar et al., Diagno Microbiol. Infect. Dis. 21 129-133, 1995.*

Metha et al., Journal of the Institution of Chemists (India),(1987) 59(4),183-185.*

DE 606497, CA 29, 12267, 1935. CAPLUS Abstract.*

Arvidsson, PI et al (2001) on the antimicrobial and hemolytic activities of amphiphilic β-peptides Chem Bio Chem 2(10):771-773.

Boman, HG (2003) Antibacterial peptides: basic facts and emerging concepts J. Intern. Med. 254(3):197-215.

Brogden, KA et al (2003) Antimicrobial peptides in animals and their role in host defences Int. J. Antimicrob Agents 22(5):465-478.

Fischetti, VA (2003) Novel method to control pathogenic bacteria on human mucous membranes Ann NY Acad Sci 987:207-214.

Giacometti, A et al (1998) In vitro activities of membrane-active peptides against gram-positive and gram-negative aerobic bacteria Antimicrobial Agents and Chemotherapy 42(12):3320-3324.

Giacometti, A et al (1999) Antimicrobial activity of polycationic peptides Peptides 20(11):1265-1273.

Goodson, B et al (1999) Characterization of novel antimicrobial peptoids Antimicrobial Agents and Chemotherapy 43(6):1429-1434.

Hancock, RE (1999) Host defence (cationic) peptides: what is their future clinical potential? Drugs 57(4):469-473.

Huang, HW (2000) Action of antimicrobial peptides: two-state model Biochemistry 39(29):8347-8352.

Liu, Z et al (2007) Length effects in antimicrobial peptides of the (RW)n Series Antimicrobial Agents and Chemotherapy 51(2):597-603.

Medzhitov, R et al (2000) Innate immune recognition: mechanisms and pathways Immunol. Rev. 173:89-97.

Rennie, J et al (2005) Simple oligomers as antimicrobial peptide mimics J Industrial Microbiol & Biotech 32(7):296-300.

Silen, JL et al (1998) Screening for novel antimicrobials from encoded combinatorial libraries by using a two-dimensional agar format Antimicrobial Agents and Chemotherapy 42(6):1447-1453.

Strøm, MB et al (2003) The pharmacophore of short cationic antibacterial peptides J Med Chem 46(9):1567-1570.

Yeaman, MR et al (2003) Mechanisms of antimicrobial peptide action and resistance Pharmacol Rev. 55:27-55.

Zasloff, M (2002) Antimicrobial peptides of multicellular organisms Nature 415(6870):389-395.

* cited by examiner

*Primary Examiner* — Venkataraman Balasubramanian

(74) *Attorney, Agent, or Firm* — Klauber & Jackson LLC

(57) ABSTRACT

Novel s-triazine compounds are disclosed that have a formula represented by the following:

I

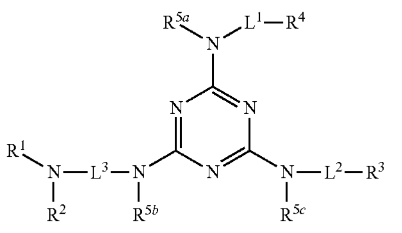

$L^1$, $L^2$, $L^3$, $R^1$, $R^2$, $R^3$, $R^4$, $R^{5a}$, $R^{5b}$, and $R^{5c}$ are as described herein. The compounds may be prepared as pharmaceutical compositions, and may be used for the prevention and treatment of a variety of conditions in mammals including humans, where microbial infection is either a direct cause or a related condition.

25 Claims, 2 Drawing Sheets

Total planktonic cell growth measured at $OD_{600}$

Bottom biofilm measured at $OD_{540}$

Total biofilm measured at $OD_{540}$

S-TRIAZINE COMPOUNDS, PHARMACEUTICAL COMPOSITIONS AND METHODS OF USING THE SAME

RELATED APPLICATION

The present application claims the benefit under 35 U.S.C. §119 of U.S. Provisional Application Ser. No. 61/314,991 filed Mar. 17, 2010, the contents of which application is hereby incorporated by reference in its entirety.

FIELD OF THE INVENTION

This invention relates to novel compositions containing active s-triazine compounds, and particularly, such s-triazine compounds as demonstrate antimicrobial, antifungal or antiviral activity. The invention also relates to methods for the preparation of the peptide compositions, and their use in preventing and/or treating conditions resulting from the unwanted presence of microbial, fungal or viral activity.

BACKGROUND OF THE INVENTION

As multidrug-resistant bacterial strains emerge in increasing numbers, the need for new kinds of antibiotics is growing. For the last few decades it has been found that a wide range of antimicrobial peptides are secreted by multicellular organisms in response to infection by foreign bacteria, viruses, or fungi (1-4). These form part of the innate immune response to infection, which is short term and fast acting relative to humoral immunity (3). These peptides have been considered as prospective antibiotic agents because their effect is rapid, broad spectrum and indifferent to resistance to standard antibiotics such as penicillin (5-6). Antimicrobial peptides differ dramatically in size, sequence and structure, apparently sharing only amphipathic character and positive charge (1, 5). The proposed mechanisms of action of antimicrobial peptides commonly focus on the interaction between these peptides and the plasma membrane of bacterial cells, even though many antimicrobial peptides also employ more sophisticated mechanisms (7). Recently, the pharmocophore of short cationic antimicrobial peptides has been extensively studied and the results showed that short cationic peptides consisting of only Arginine (R) and Tryptophan (W) could serve as moderately effective antimicrobial agents (8-9).

Besides various advantages over conventional antibiotics, the practical use of antimicrobial peptides, however, are limited by many factors. These peptides are usually more expensive to make, are vulnerable to protease degradation, and have relatively high toxicity. A number of normatural peptides built from beta-amino acids or peptoids, as well as other peptide mimics have been studied in order to overcome these problems (10-12). For example, the present inventor previously designed and screened inexpensive small compounds to mimic the hydrophobic-cationic pattern observed in the pharmocophore of small cationic antimicrobial peptides using 1,3,5-triazine as a template. Previous studies showed that possible antimicrobials could be identified through combinatorial libraries constructed to have varieties of tri-substituted 1,3,5-triazines (13).

US patent application Publication No. US2009/03259666 discloses s-triazine compounds having microbial properties.

From the above, it remains that a continuing need exists for the stepwise design and optimization of different functional groups (mainly hydrophobic, bulky or charged groups) on the triazine scaffold in search of potential new antimicrobials, as well as to gain insight as to the structure-function relationship of these agents.

Furthermore, it remains that a continuing need exists for the development of modalities that can deliver effective antibiotic s-triazine compounds in a manner that confers both improved stability and economy of the therapeutic, but importantly, significantly improves the therapeutic efficacy and strength of the resultant molecule. It is toward the fulfillment of these and other related objectives that the present invention is directed.

SUMMARY OF THE INVENTION

As set forth earlier herein, the present invention relates to s-triazine compounds, pharmaceutical compositions thereof and their use as antimicrobial/antiviral/antifungal compounds.

The present invention relates to s-triazine compounds having antimicrobial properties, according to formula I:

I

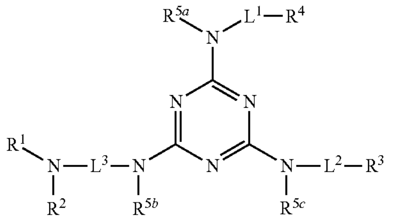

wherein each $L^1$ and $L^2$ is independently selected from a single bond, or $C_1$-$C_4$ alkylene;

L3 is selected from $C_2$-$C_6$ alkylene, $C_2$-$C_6$ alkenyl, and $C_2$-$C_6$ alkynyl;

each $R^1$ and $R^2$ is independently selected from hydrogen, and substituted or unsubstituted $C_1$-$C_6$ alkyl; or $R^1$ and $R^2$ may join together to form a 4-7 membered heterocycloalkyl; or $R^1$ is H; and $R^2$ is —C(=NH)—$NH_2$;

$R^3$ is $R^4$; or $R^3$ is selected from substituted or unsubstituted aryl and substituted or unsubstituted heteroaryl;

$R^4$ is substituted or unsubstituted

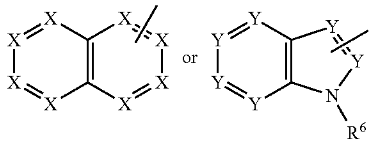

each X is C or N; provided no more than three Xs are N at one time;

each Y is C or N; provided no more than three Ys are N at one time;

$R^6$ is H or substituted or unsubstituted $C_1$-$C_6$ alkyl;

each $R^{5a}$, $R^{5b}$, or $R^{5c}$ is independently H or substituted or unsubstituted $C_1$-$C_6$ alkyl;

or a pharmaceutically acceptable salt, solvate or prodrug thereof;

and stereoisomers, isotopic variants and tautomers thereof.

In one embodiment, with respect to compounds of formula I, each $R^{5a}$, $R^{5b}$, or $R^{5c}$ is independently H.

In one particular embodiment, with respect to compounds of formula Ia, $R^4$ is substituted or unsubstituted

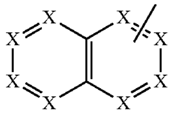

each X is C or N; provided that no more than three Xs are N at one time.

In another particular embodiment, with respect to compounds of formula I, $R^4$ is substituted or unsubstituted

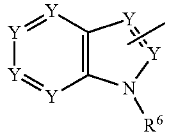

each Y is C or N; provided that no more than three Ys are N at one time;

$R^6$ is H or substituted or unsubstituted $C_1$-$C_6$ alkyl.

In a further aspect, the present invention provides the method for the preparation of the s-triazine compounds of the invention.

In a further aspect, the s-triazine compounds of the invention may be used to treat microbial or fungal conditions affecting lower animals, and possibly, plants. The s-triazine compounds could be designed and assembled to include the s-triazine compounds pertinent for the treatment of a particular microbe or fungus of interest, and then formulated into appropriate compositions and dosage forms for administration or application to an affected host.

In a further aspect, the present invention provides pharmaceutical compositions comprising a peptide of the invention, and a pharmaceutical carrier, excipient or diluent. In this aspect of the invention, the pharmaceutical composition can comprise one or more variant s-triazine compounds of the invention, prepared, for example, with a differing array of peptide linkers, to afford a more comprehensive treatment in the instance where a multiplicity of microbial/viral/fungal antigens are known to be present.

In a further aspect of the invention, a method is disclosed for treating mammals, including humans, as well as lower mammalian species, susceptible to or afflicted with a condition attributable to or resulting from a microbial, viral or fungal infection, which method comprises administering an effective amount of a pharmaceutical composition containing or comprising the s-triazine compounds just described.

Another aspect of this invention relates to the use of the compounds of the invention in a therapeutic method, a pharmaceutical composition, and the manufacture of such composition, useful for the treatment of conditions attributable to or resulting from a microbial, viral or fungal infection.

In additional aspects, this invention provides methods for synthesizing the compounds of the invention, with representative synthetic protocols and pathways disclosed later on herein.

In further additional aspects, this invention provides methods for synthesizing polymeric triazines for surface coatings.

Other objects and advantages will become apparent to those skilled in the art from a consideration of the ensuing detailed description, which proceeds with reference to the following illustrative drawings.

DETAILED DESCRIPTION OF THE INVENTION

Definitions

Figure 1:
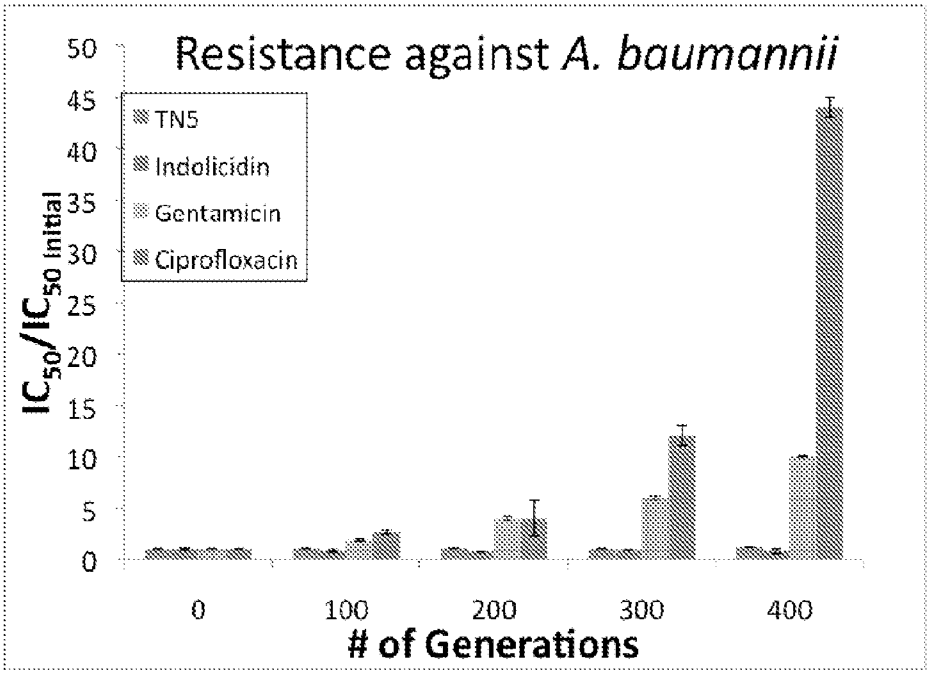
FIG. 1 graphically depicts the experimental evaluation of the ability of *A. baumannii* to evolve resistance to sublethal TN5 and the AMP indolicidin relative to two antibiotics in current use. Changes in the $IC_{50}$ of cultures exposed to sublethal doses of TN5 are expressed as ratios of the new to original values. For reference, the response of these cells to two current antibiotics is shown. In the latter cases, there is a significant increase in the $IC_{50}$ on 400 generations of exposure.
Figure 2:
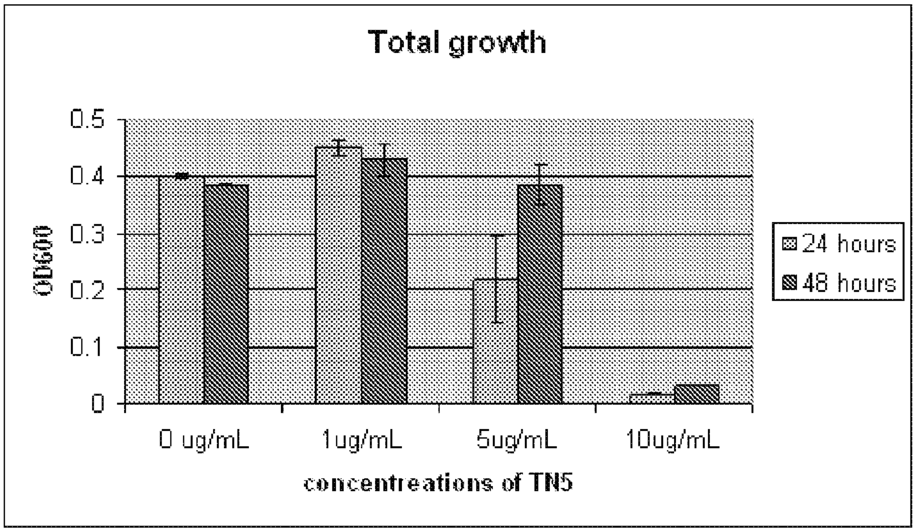
FIG. 2 shows the total planktonic cell growth measured at $OD_{600}$.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —N$R^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Alkoxy" refers to the group —$OR^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Alkoxycarbonylamino" refers to the group —$NR^{25}C(O)OR^{26}$, where $R^{25}$ is hydrogen, alkyl, aryl or cycloalkyl, and $R^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-$S(O)_2$—, and aryl-$S(O)_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—$CH{=}CH_2$), n-propenyl (—$CH_2CH{=}CH_2$), isopropenyl (—$C(CH_3){=}CH_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —$CH{=}CHCH_2$— and —$C(CH_3){=}CH$— and —$CH{=}C(CH_3)$—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2C{\equiv}CH$), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-$S(O)_2$— and aryl-$S(O)_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical $—NO_2$.

"Substituted" refers to a group in which one or more hydrogen atoms are each independently replaced with the same or different substituent(s). Typical substituents include, but are not limited to —X, $—R^{46}$, —O—, ═O, $—OR^{46}$, $—SR^{46}$, $—S^-$, ═S, $—NR^{46}R^{47}$, $═NR^{46}$, $—CX_3$, $—CF_3$, —CN, —OCN, —SCN, —NO, $—NO_2$, $═N_2$, $—N_3$, $—S(O)_2O^-$, $—S(O)_2OH$, $—S(O)_2R^{46}$, $—OS(O_2)O^-$, $—OS(O)_2R^{46}$—P$(O)(O^-)_2$, $—P(O)(OR^{46})(O)$, $—OP(O)(OR^{46})(OR^{47})$, $—C(O)R^{46}$, $—C(S)R^{46}$, $—C(O)OR^{46}$, $—C(O)NR^{46}R^{47}$, $—C(O)O^-$, $—C(S)OR^{46}$, $—NR^{48}C(O)NR^{46}R^{47}$, $—NR^{49}C(NR^{48})NR^{46}R^{47}$ and $—C(NR^{48})NR^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, $—NR^{50}R^{51}$, $—C(O)R^{50}$ or $—S(O)_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following:

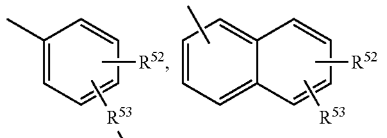

and

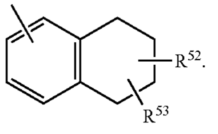

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{54}COR^{55}$, $NR^{54}SOR^{55}$, $NR^{54}SO_2R^{57}$, COOalkyl, COOaryl, $CONR^{54}R^{55}$, $CONR^{54}OR^{55}$, $NR^{54}R^{55}$, $SO_2NR^{54}R^{55}$, S-alkyl, S-alkyl, SOalkyl, $SO_2$alkyl, Saryl, SOaryl, $SO_2$aryl; or $R^{52}$ and $R^{53}$ may be joined to form a cyclic ring (saturated or unsaturated) from 5 to 8 atoms, optionally containing one or more heteroatoms selected from the group N, O or S, $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

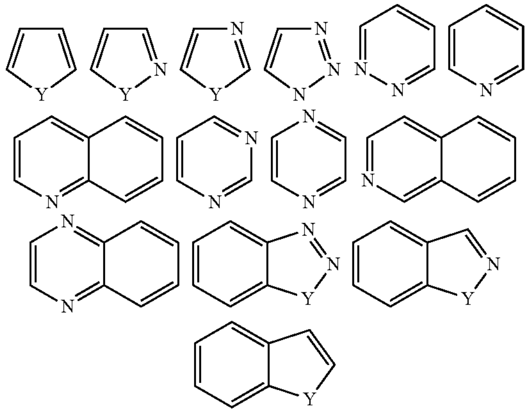

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

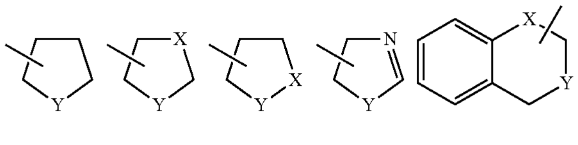

-continued

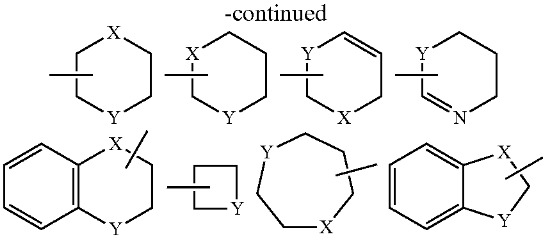

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—. Substituting groups include carbonyl or thiocarbonyl which provide, for example, lactam and urea derivatives.

Examples of representative cycloheteroalkenyls include the following:

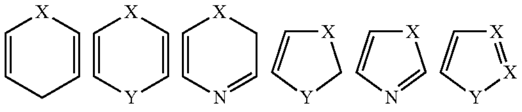

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

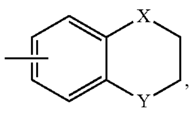, 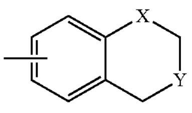 and

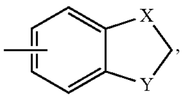, wherein each X is selected from C—$R^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R group present as substituents directly on the ring atoms of the compounds provided herein or may be present as a substituent in the "substituted" aryl and aliphatic groups present in the compounds.

Examples of hetero substituents include:

-halo,

—$NO_2$, —$NH_2$, —$NHR^{59}$, —$N(R^{59})_2$,

—NRCOR, —$NR^{59}SOR^{59}$, —$NR^{59}SO_2R^{59}$, OH, CN,

—$CO_2H$,

—$R^{59}$—OH, —O—$R^{59}$, —$COOR^{59}$,

—$CON(R^{59})_2$, —$CONROR^{59}$,

—$SO_3H$, —$R^{59}$—S, —$SO_2N(R^{59})_2$,

—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containing O—H, or N—H functionality. Examples of "hydrogen bond donor" groups include —OH, —$NH_2$, and —NH—$R^{59a}$ and wherein $R^{59a}$ is alkyl, acyl, cycloalkyl, aryl, or heteroaryl.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)$NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Sulfanyl" refers to the radical HS—. "Substituted sulfanyl" refers to a radical such as RS— wherein R is any substituent described herein.

"Sulfonyl" refers to the divalent radical —$S(O_2)$—. "Substituted sulfonyl" refers to a radical such as $R^{61}$—$(O_2)$S— wherein $R^{61}$ is any substituent described herein. "Aminosulfonyl" or "Sulfonamide" refers to the radical $H_2N(O_2)S$—, and "substituted aminosulfonyl" or "substituted sulfonamide" refers to a radical such as $R^{62}_2N(O_2)S$— wherein each $R^{62}$ is independently any substituent described herein.

"Sulfone" refers to the group —$SO_2R^{63}$. In particular embodiments, $R^{63}$ is selected from H, lower alkyl, alkyl, aryl and heteroaryl.

"Thioaryloxy" refers to the group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound provided herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound provided herein is administered.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Tautomers" refer to compounds that are interchangeable forms of a particular compound structure, and that vary in the displacement of hydrogen atoms and electrons. Thus, two structures may be in equilibrium through the movement of $\pi$ electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H$/D, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$ and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure 5-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds provided herein may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The S-Triazine Compounds

As set forth earlier herein, the s-triazine compounds comprise antimicrobial/antiviral/antifungal s-triazine compounds. The s-triazine compounds may have a lethal effect on bacteria, viruses or fungi in its monomeric form. More particularly, the s-triazine compounds may be any antimicrobial s-triazine compounds, including natural products found in organisms, fragments of natural s-triazine compounds, and any synthetic analogs or de novo designs. These s-triazine compounds can accordingly include normatural amino acids: beta-amino acids, d-amino acids and/or non-indigenous amino acids.

The present invention relates to s-triazine compounds having antimicrobial properties, according to formula I:

I

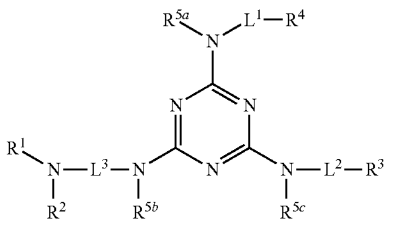

wherein each $L^1$ and $L^2$ is independently selected from a single bond, or $C_1$-$C_4$ alkylene;

L3 is selected from $C_2$-$C_6$ alkylene, $C_2$-$C_6$ alkenyl, and $C_2$-$C_6$ alkynyl;

each $R^1$ and $R^2$ is independently selected from hydrogen, and substituted or unsubstituted $C_1$-$C_6$ alkyl; or $R^1$ and $R^2$ may join together to form a 4-7 membered heterocycloalkyl; or $R^1$ is H; and $R^2$ is —C(═NH)—$NH_2$;

$R^3$ is $R^4$; or $R^3$ is selected from substituted or unsubstituted aryl and substituted or unsubstituted heteroaryl;

$R^4$ is substituted or unsubstituted

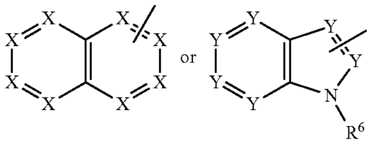

each X is C or N; provided that no more than three Xs are N at one time;

each Y is C or N; provided that no more than three Ys are N at one time;

$R^6$ is H or substituted or unsubstituted $C_1$-$C_6$ alkyl;

each $R^{5a}$, $R^{5b}$, or $R^{5c}$ is independently H or substituted or unsubstituted $C_1$-$C_6$ alkyl;

or a pharmaceutically acceptable salt, solvate or prodrug thereof;

and stereoisomers, isotopic variants and tautomers thereof.

In one embodiment, with respect to the compounds of formula I, each $R^{5a}$, $R^{5b}$, or $R^{5c}$ is independently H. In another embodiment, each $R^{5a}$, $R^{5b}$, or $R^{5c}$ is independently $C_1$-$C_6$ alkyl.

In one embodiment, with respect to the compounds of formula I, the compound is according to formula II:

II

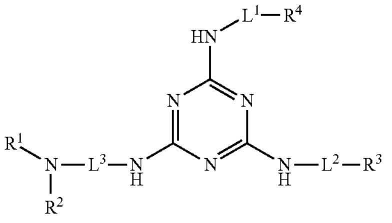

wherein $L^1$, $L^2$, $L^3$, $R^1$, $R^2$, $R^3$ and $R^4$ are as described for formula I;

or a pharmaceutically acceptable salt, solvate or prodrug thereof;

and stereoisomers, isotopic variants and tautomers thereof.

In one embodiment, with respect to the compounds of formulae I-II, $R^4$ is substituted or unsubstituted

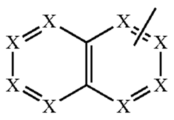

each X is C or N; provided that no more than three Xs are N at one time.

In one embodiment, $R^4$ is as described above; and one of the Xs is N.

In another embodiment, $R^4$ is as described above; and two of the Xs are N.

In yet another embodiment, with respect to the compounds of formulae I-II, $R^4$ is substituted or unsubstituted naphthalenyl, quinolinyl, isoquinolinyl, naphthyridinyl, quinazolinyl, quinoxalinyl, phthalazinyl, or cinnolinyl.

In yet another embodiment, with respect to the compounds of formulae I-II, $R^4$ is naphthalenyl, quinolinyl, isoquinolinyl, naphthyridinyl, quinazolinyl, quinoxalinyl, phthalazinyl, or cinnolinyl, unsubstituted or substituted with one or more alkyl, halo, haloalkyl, carboxy, amino, or cyano.

In yet another embodiment, with respect to the compounds of formulae I-II, $R^4$ is naphthalenyl, quinolinyl, isoquinolinyl, naphthyridinyl, quinazolinyl, quinoxalinyl, phthalazinyl, or cinnolinyl, unsubstituted or substituted with one or more of Me, Et, Cl, F, CN, COOH, or $CF_3$.

In yet another embodiment, with respect to the compounds of formulae I-II, $R^4$ is substituted or unsubstituted

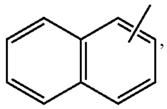, 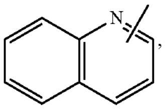, 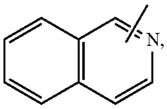,
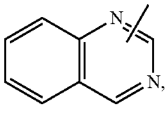, 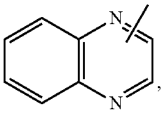, 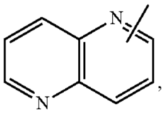,
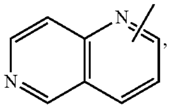, 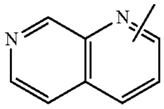 or 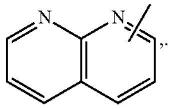.

In yet another embodiment, with respect to the compounds of formulae I-II, $R^4$ is

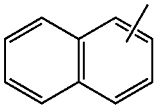, 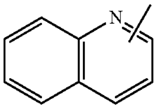, 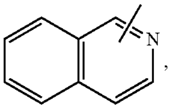,
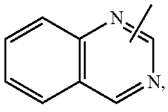, 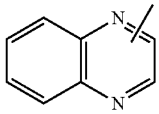, 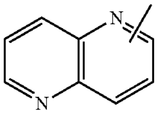,
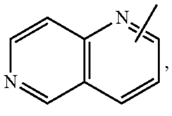, 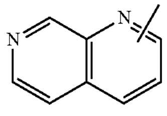 or 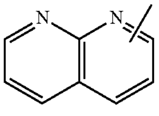;

unsubstituted or substituted with one or more alkyl, halo, haloalkyl, amino, carboxy, or cyano.

In yet another embodiment, with respect to the compounds of formulae I-II, $R^4$ is

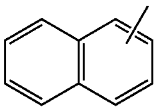, 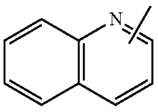, 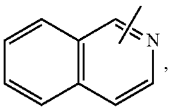,

-continued

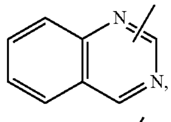 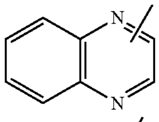, 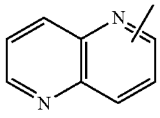,

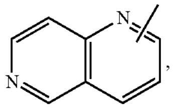, 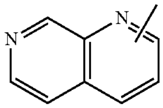 or 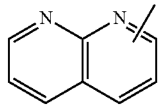;

unsubstituted or substituted with one or more of Me, Et, Cl, F, CN, COOH, or $CF_3$.

In one particular embodiment, with respect to the compounds of formulae I-II, $R^4$ is

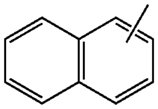;

unsubstituted or substituted with one or more of alkyl, halo, haloalkyl, amino, carboxy, or cyano.

In another particular embodiment, with respect to the compounds of formulae I-II, $R^4$ is

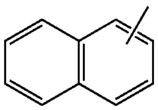;

unsubstituted or substituted with one or more of Me, Et, Cl, F, CN, COOH, or $CF_3$.

In a more particular embodiment, with respect to the compounds of formulae I-II, $R^4$ is unsubstituted

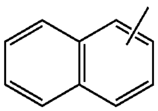.

In one embodiment, with respect to the compounds of formulae I-II, $R^4$ is substituted or unsubstituted

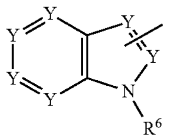

each Y is C or N; provided that no more than three Ys are N at one time;

$R^6$ is H or substituted or unsubstituted $C_1$-$C_6$ alkyl.

In another embodiment, with respect to the compounds of formulae I-II, $R^4$ is indolyl, imidazolyl, or pyridopyrrolidinyl, unsubstituted or substituted with one or more of alkyl, halo, haloalkyl, amino, carboxy, or cyano.

In yet another embodiment, with respect to the compounds of formulae I-II, $R^4$ is indolyl, imidazolyl, or pyridopyrrolidinyl, unsubstituted or substituted with one or more Me, Et, Cl, F, CN, COOH, or $CF_3$.

In one particular embodiment, with respect to the compounds of formulae I-II, $R^4$ is substituted or unsubstituted

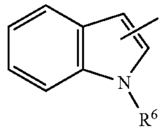

$R^6$ is H or substituted or unsubstituted $C_1$-$C_6$ alkyl.

In one embodiment, $R^4$ is as described above; and $R^6$ is H.

In one embodiment, with respect to the compounds of formula I, the compound is according to formula IIIa or IIIb:

IIIa

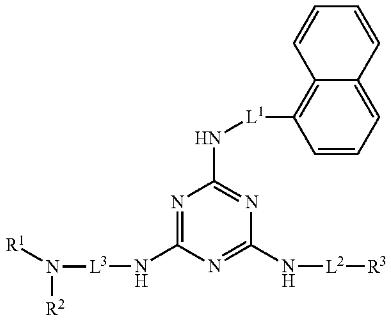 or

IIIb

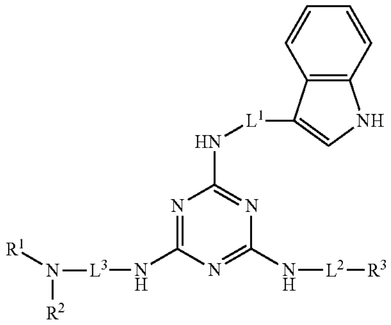

wherein $L^1$, $L^2$, $L^3$, $R^1$, $R^2$, and $R^3$ are as described for formula I;

or a pharmaceutically acceptable salt, solvate or prodrug thereof; and stereoisomers, isotopic variants and tautomers thereof.

In one embodiment, with respect to the compounds of formulae I-IIIb, $L^1$ is a single bond, $-CH_2-$, or $CH_2-CH_2-$.

In one particular embodiment, with respect to the compounds of formulae I-IIIb, $L^1$ is $-CH_2-$, or $CH_2-CH_2-$.

In one embodiment, with respect to the compounds of formula I, the compound is according to formula IVa, IVb, IVc, or IVd:

IVa

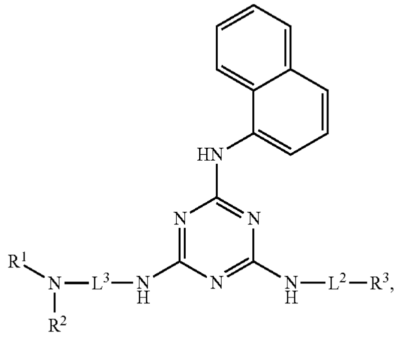

-continued

IVb

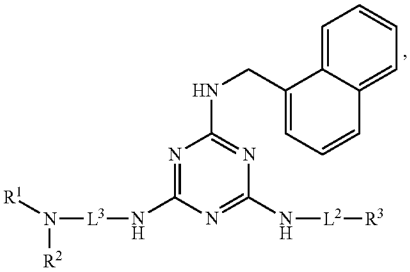

IVc

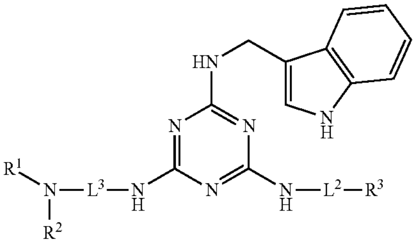

or

IVd

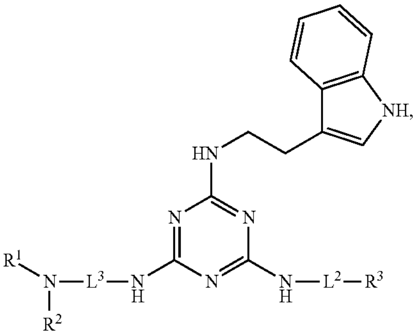

wherein $L^2$, $L^3$, $R^1$, $R^2$, and $R^3$ are as described for formula I;

or a pharmaceutically acceptable salt, solvate or prodrug thereof;

and stereoisomers, isotopic variants and tautomers thereof.

In one embodiment, with respect to the compounds of formulae I-IVd, $R^3$ is $R^4$; and $R^4$ is as described herein.

In another embodiment, with respect to the compounds of formulae I-IVd, $R^3$ is phenyl, naphthyl, pyridyl, indolyl, or quinolinyl, unsubstituted or substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamide.

In yet another embodiment, with respect to the compounds of formulae I-IVd, $R^3$ is phenyl, naphthyl, pyridyl, indolyl, or quinolinyl, unsubstituted or substituted with one or more substituents independently selected from Me, Et, OH, Cl, F, CN, $SO_2Me$, COOH, and $CF_3$.

In one particular embodiment, with respect to the compounds of formulae I-IVd, $R^3$ is phenyl.

In one particular embodiment, with respect to the compounds of formula I, the compound is according to formula Va, Vb, Vc, or Vd:

Va

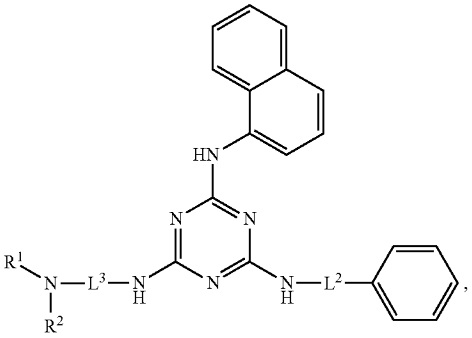

Vb

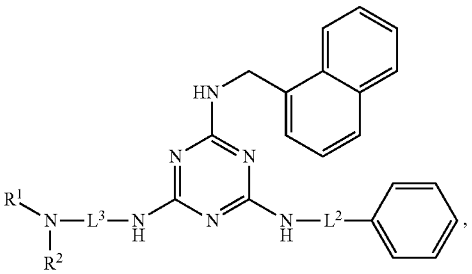

Vc

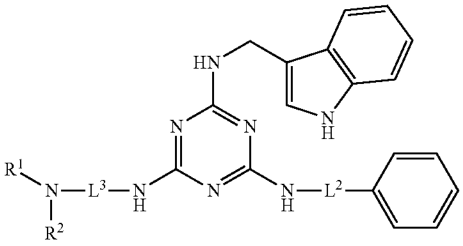

or

Vd

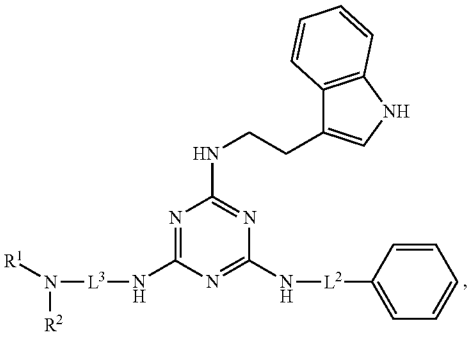

wherein $L^2$, $L^3$, R', and $R^2$ are as described for formula I;

or a pharmaceutically acceptable salt, solvate or prodrug thereof;

and stereoisomers, isotopic variants and tautomers thereof.

In another particular embodiment, with respect to the compounds of formula I, the compound is according to formula VIa, VIb, VIc, or VId:

VIa

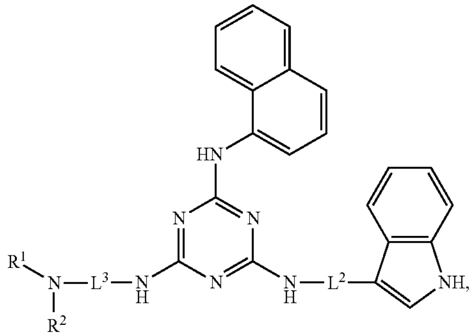

VIb

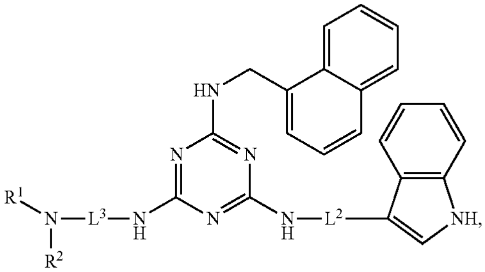

VIc

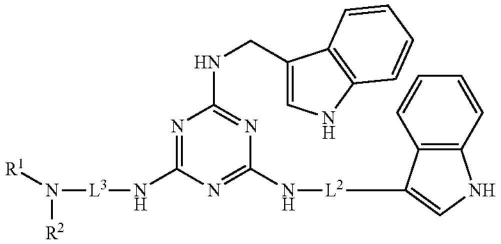

or

VId

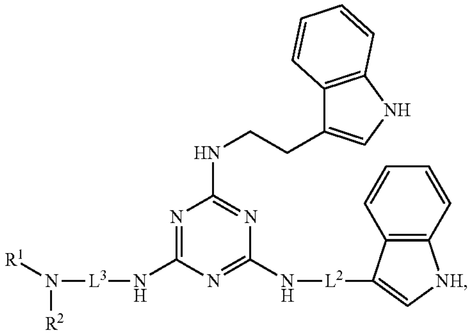

wherein $L^2$, $L^3$, $R^1$, and $R^2$ are as described for formula I;

or a pharmaceutically acceptable salt, solvate or prodrug thereof;

and stereoisomers, isotopic variants and tautomers thereof.

In one embodiment, with respect to the compounds of formulae I-VId, $L^2$ is a single bond, $—CH_2—$, or $CH_2—CH_2—$.

In one particular embodiment, with respect to the compounds of formulae I-VId, $L^2$ is $—CH_2—$, or $CH_2—CH_2—$.

In one embodiment, with respect to the compounds of formula I, the compound is according to formula VIIa, VIIb, VIIc, or VIId:

VIIa

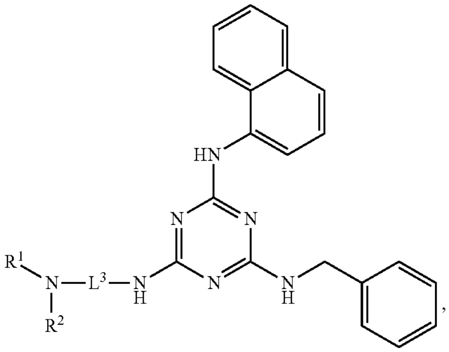

VIIb

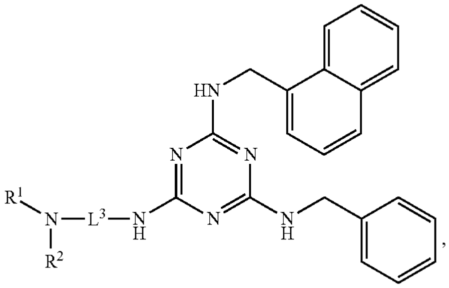

VIIc

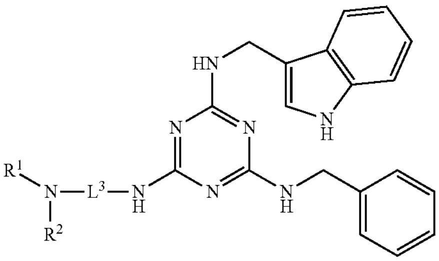

or

VIId

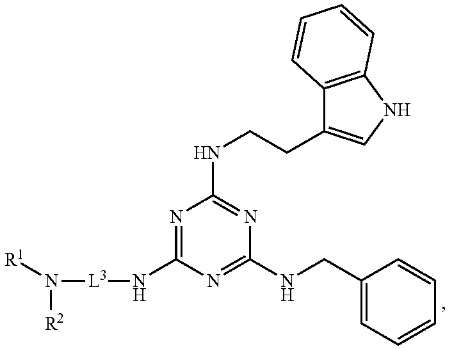

wherein $L^3$, $R^1$, and $R^2$ are as described for formula I;

or a pharmaceutically acceptable salt, solvate or prodrug thereof;

and stereoisomers, isotopic variants and tautomers thereof.

In one embodiment, with respect to the compounds of formula I, the compound is according to formula VIII:

VIII

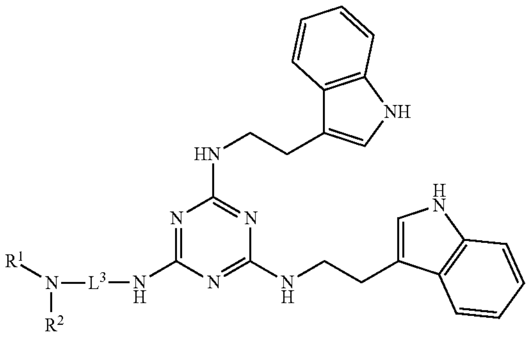

wherein $L^3$, $R^1$, and $R^2$ are as described for formula I;

or a pharmaceutically acceptable salt, solvate or prodrug thereof;

and stereoisomers, isotopic variants and tautomers thereof.

In one embodiment, with respect to the compounds of formulae I-VIII, $L^3$ is $-CH_2-$, $-CH_2-CH_2-$, $-CH_2-CH_2-CH_2-$, or $-CH_2-CH_2-CH_2-CH_2-$.

In another embodiment, with respect to the compounds of formulae I-VIII, $L^3$ is $-CH_2-CH{=}CH-CH_2-$.

In yet another embodiment, with respect to the compounds of formulae I-VIII, $L^3$ is $-CH_2-C{\equiv}C-CH_2-$.

In one embodiment, with respect to the compounds of formulae I-VIII, each $R^1$ and $R^2$ is independently selected from hydrogen. In another embodiment, each $R^1$ and $R^2$ is substituted or unsubstituted $C_1$-$C_6$ alkyl.

In yet another embodiment, each $R^1$ is H; and $R^2$ is $-C({=}NH)-NH_2$.

In one particular embodiment, with respect to the compounds of formulae I-VIII, each $R^1$ and $R^2$ is independently hydrogen.

In another particular embodiment, with respect to the compounds of formulae I-VIII, each $R^1$ and $R^2$ is independently substituted or unsubstituted $C_1$-$C_6$ alkyl.

In another embodiment, with respect to the compounds of formulae I-VIII, each $R^1$ and $R^2$ is independently Me, Et, n-Pr, i-Pr, or n-Bu.

In a more particular embodiment, with respect to the compounds of formulae I-VIII, each $R^1$ and $R^2$ is n-Bu.

In a further particular embodiment, with respect to the compounds of formulae I-VIII, $R^1$ is H; and $R^2$ is $-C({=}NH)-NH_2$.

In one embodiment, with respect to the compounds of formula I, the compound is according to formula IXa, IXb, IXc, or IXd:

IXa

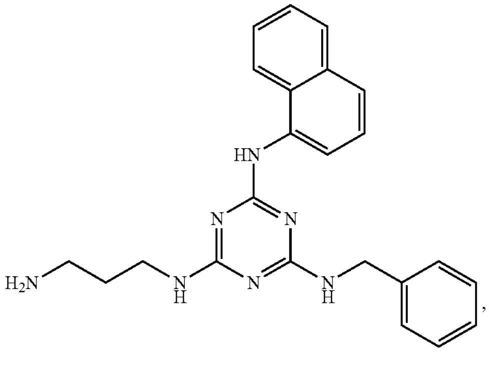

-continued

IXb

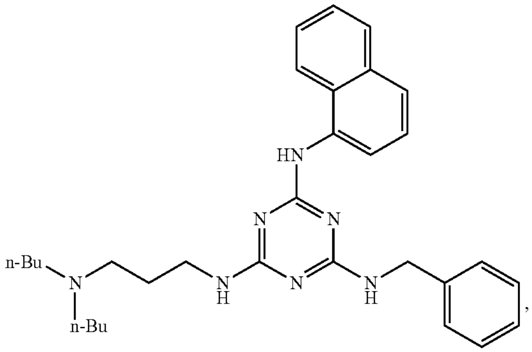

IXc

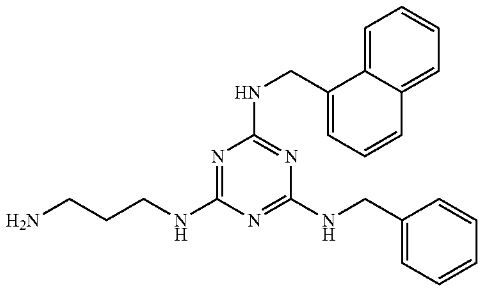

or

IXd

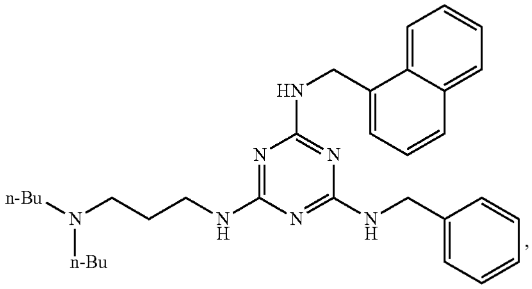

or a pharmaceutically acceptable salt, solvate or prodrug thereof;

and stereoisomers, isotopic variants and tautomers thereof.

In one embodiment, with respect to the compounds of formula I, the compound is according to formula Xa, Xb, or Xc:

Xa

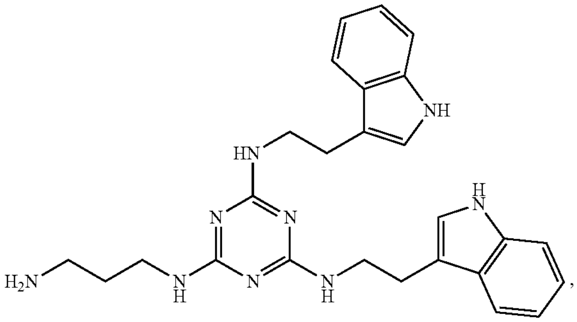

-continued
Xb
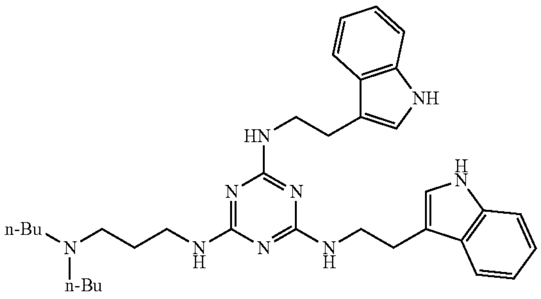
or
Xc
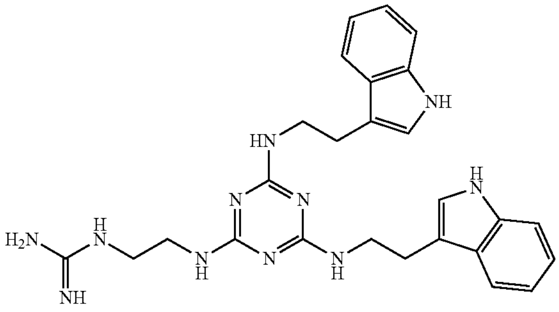
,
or a pharmaceutically acceptable salt, solvate or prodrug thereof;
and stereoisomers, isotopic variants and tautomers thereof.
In one particular aspect the invention provides s-triazines selected from
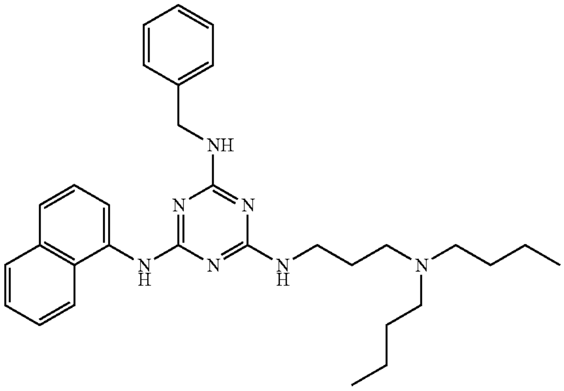
TN-2
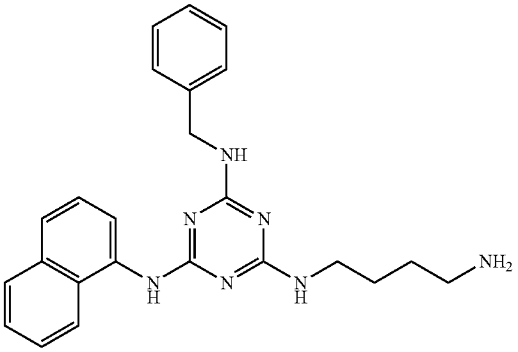
TN-3
-continued
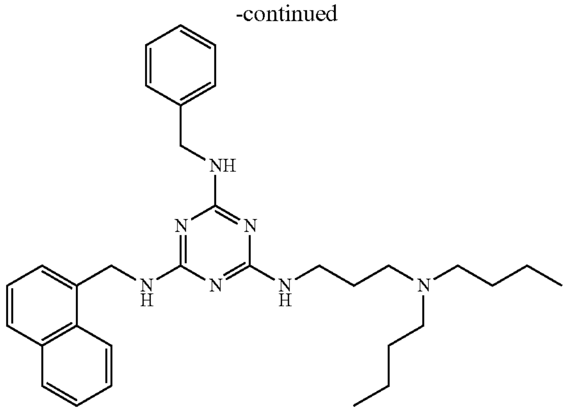
TN-4
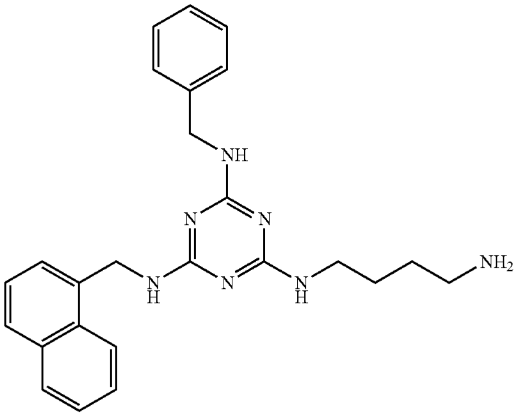
TN-5
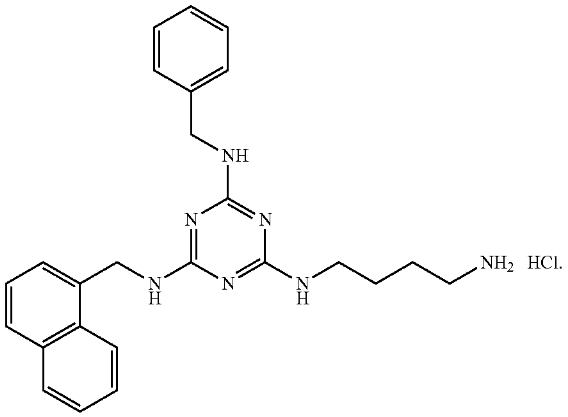
TN-5 HCl
In another particular aspect the invention provides s-triazines selected from

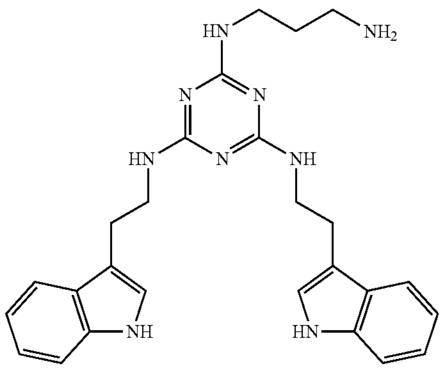

TZ-WKW

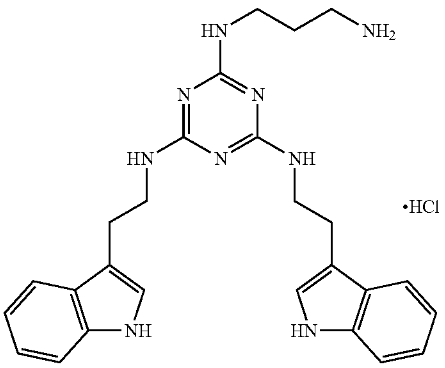

TZ-WKW HCl salt

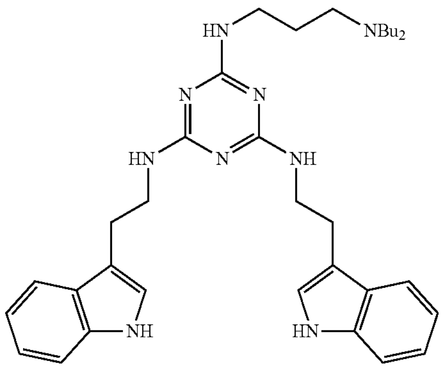

TZ-WK(Bu)2W

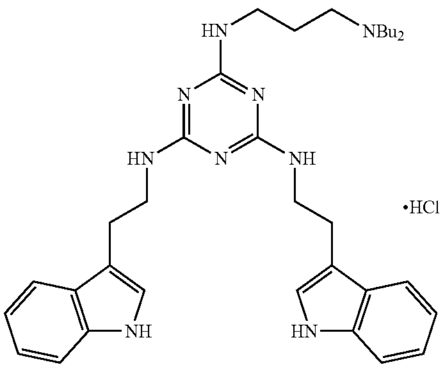

TZ-WK(Bu)2W HCl salt

-continued

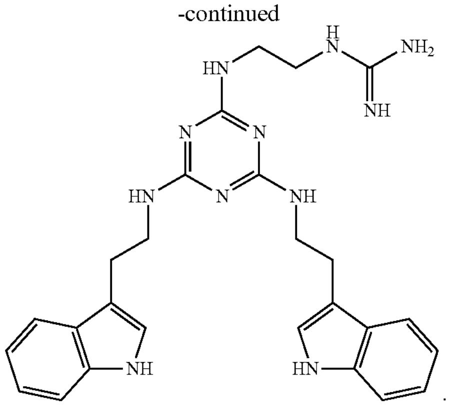

TZ-WRW

In more particular aspect the invention provides the s-triazine compound depicted by formula TN-5.

In another aspect the invention provides a method for preventing, treating, ameliorating or managing a disease or condition which comprises administering to a patient in need of such prevention, treatment, amelioration or management, a prophylactically or therapeutically effective amount of the pharmaceutical composition of s-triazines of formula I.

In one embodiment, with respect to the method, the disease or condition is or results from a bacterial infection. In another embodiment, the disease or condition is or results from a viral infection. In a yet another embodiment, the disease or condition is or results from a fungal infection.

In a further aspect the invention provides a method for preventing, treating, ameliorating or managing a disease or condition, which comprises administering to a patient in need of such prevention, treatment, amelioration or management a prophylactically or therapeutically acceptable amount of s-triazines of formula I, or the pharmaceutical composition of thereof, wherein the disease or condition results from or is caused by bacterial infection, viral infection or fungal infection.

In certain aspects and where appropriate, the present invention extends to the preparation of prodrugs and derivatives of the compounds of the invention. Prodrugs are derivatives which have cleavable groups and become by solvolysis or under physiological conditions the compounds of the invention, which are pharmaceutically active, in vivo.

In further additional aspects, this invention provides methods for synthesizing polymeric triazines for surface coatings. These polymeric triazines can be prepared by the conjugation reaction between polymeric anhydride (PMA) and triazine compound of the invention.

Pharmaceutical Compositions

When employed as pharmaceuticals, the triazine compounds of this invention are typically administered in the form of a pharmaceutical composition. Such compositions can be prepared in a manner well known in the pharmaceutical art and comprise at least one active compound.

Generally, the triazine compounds of this invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds and compositions of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds and compositions of the invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds may be used as therapeutic agents for the treatment of conditions in mammals. Accordingly, the compounds and pharmaceutical compositions of this invention find use as therapeutics for preventing and/or treating infections and like maladies resulting from bacterial, viral or fungal attack, and related conditions in mammals, including humans. Thus, and as stated earlier, the present invention includes within its scope, and extends to, the recited methods of treatment, as well as to the compounds and compositions of the invention for use in such methods, and for the preparation of medicaments useful for such methods.

In a method of treatment aspect, this invention provides a method of treating a mammal susceptible to or afflicted with a condition associated with or resulting from bacterial, viral or fungal attack or infection, which method comprises administering an effective amount of one or more of the pharmaceutical compositions just described.

In additional method of treatment aspects, this invention provides methods of treating a mammal susceptible to or afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The compounds of this invention can be administered as the sole active agent or they can be administered in combination with other agents, including other active derivatives.

General Synthetic Procedures

The compounds of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative s-triazine compounds that have been listed hereinabove. The s-triazine compounds of the invention may be prepared from known or commercially available starting materials and reagents by one skilled in the art of organic synthesis.

General

Unless otherwise noted, materials and solvents were obtained from commercial suppliers and were used without further purification Anhydrous tetrahydrofuran (THF) and 1-methyl-2-pyrrolidinone (NMP) from Acros were used as reaction solvents without any prior purification. PAL-aldehyde resin from Midwest Bio-Tech was used as the solid support. For the synthesis of building block I, general coupling reactions were performed through solution phase chemistry and were purified by flash column chromatography on Merck silica gel 60-$PF_{245}$. All products were identified by LC/MS from Agilent Technology using a C18 column (20×4.0 mm), with a gradient of 5-95% $CH_3CN$ (containing 1% acetic acid)-$H_2O$ (containing 1% acetic acid) as eluant.

Equipment

Thermal reactions were performed using a standard heat block from VWR scientific Products using 4 mL vials. Resin filtration procedures were carried out using 70 μPE frit cartridge from Applied Separations.

General schemes for the preparation of the s-triazines of the invention are set forth in the synthetic schemes given below.

Scheme 1

General Synthetic Scheme for the Preparation of s-Triazines of the Invention

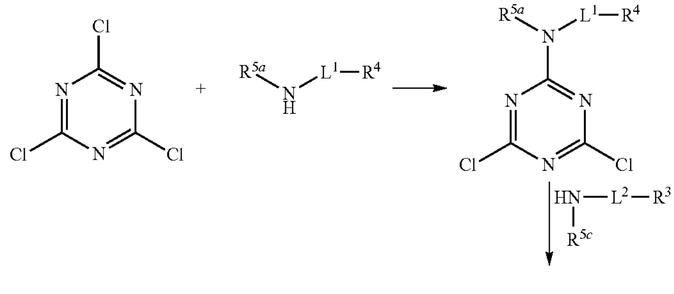

-continued

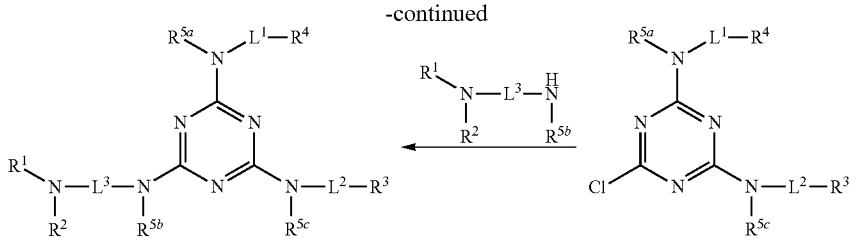

I $L^1$, $L^2$, $L^3$, $R^1$, $R^2$, $R^3$, $R^4$, $R^{5a}$, $R^{5b}$, and $R^{5c}$ are as described herein.

The s-triazines of the invention can be prepared by using solid phase or solution phase methodologies.

The general synthesis of these s-triazines is based on stepwise displacement of cyanuric chloride with $R^4$, $R^3$, and $R^2$ substituted amines, as depicted in Scheme 1.

Synthesis of a-Triazines a. Step I

Cyanuric trichloride (1 equiv.) is dissolved in THF with DIEA (10 equiv.) at 0° C. $R^4$-$L^1$-substituted amine (1.2 equiv.) in THF is added dropwise. The reaction mixture is stirred at 0° C. for 1 h. Upon completion of the reaction, the reaction mixture is quickly filtered through a plug of flash silica and washed with EA. The filtrate is evaporated in vacuo. The resulting products can be purified using flash column chromatography (particle size 32-63 μm).

b. Step II

The above amine (0.44 mmole) is added to $R^3$-$L^2$ substituted amine (0.11 mmole) in DIEA (1 mL) and anhydrous THF (10 mL) at room temperature. The reaction mixture is heated to 60° C. for 3 h and filtered. The resin is washed with DMF (5 times), alternatively with dichloromethane and methanol (5 times), and finally dichloromethane (5 times). The resin can be dried in vacuo.

c. Step III

General Procedure for the Final Amination on the Resin and Product Cleavage Reaction.

The $R^1R^2N$-$L^3$ substituted amine (4 equiv.) is added to the resin (10 mg), coupled with the above amine, in DIEA (8 μL) and 1 mL of NMP:n-BuOH (1:1). The reaction mixture is heated to 120° C. for 3 h. The resin is washed with DMF (5 times), alternatively with dichloromethane and methanol (5 times), and finally dichloromethane (5 times). The resin is dried in vacuo. The product cleavage reaction is performed using 10% trifluoroacetic acid (TFA) in dichloromethane (1 mL) for 30 min at room temperature and washed with dichloromethane (0.5 mL). Free hydroxyl containing compounds are further treated with a piperazine resin in 0.5 mL THF at room temperature for 5 h to cleave the trifluoroacetic ester that is formed upon treatment with TFA. The resin is filtered out and washed with 0.1 mL THF. The purity and identity of all the products can be monitored by LC-MS at 250 nm (Agilent Model 1100).

The series of s-triazines can be synthesized utilizing the above method and their antimicrobial activities can be tested against gram-positive bacteria *B. Subtilis*.

The following s-triazines were prepared using the methods described herein.

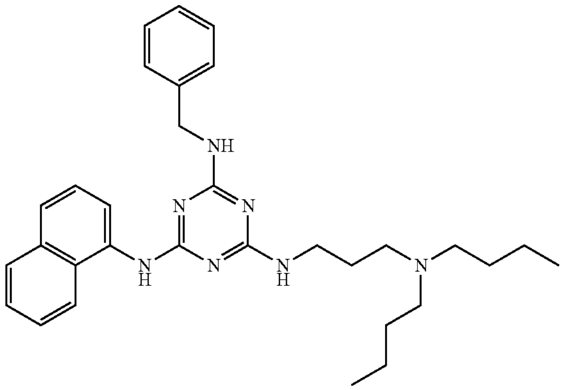

TN-2

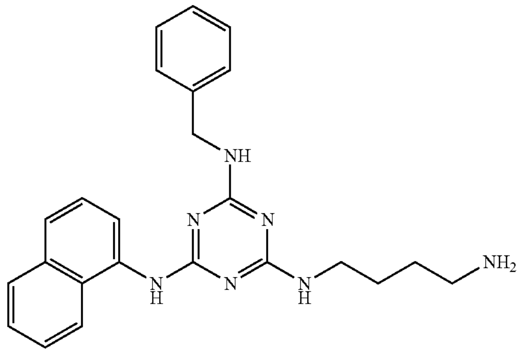

TN-3

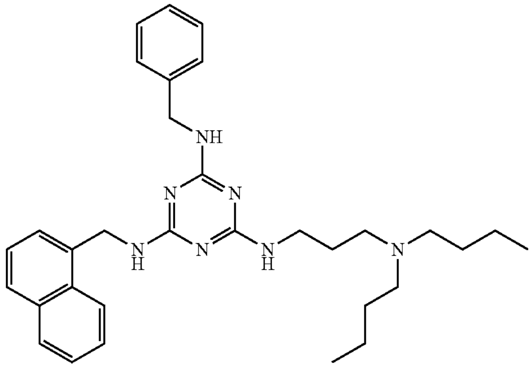

TN-4

-continued
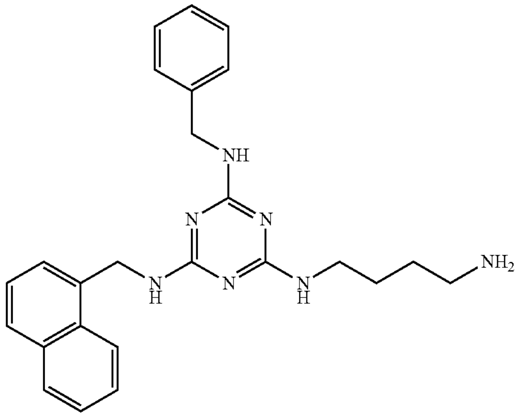
TN-5
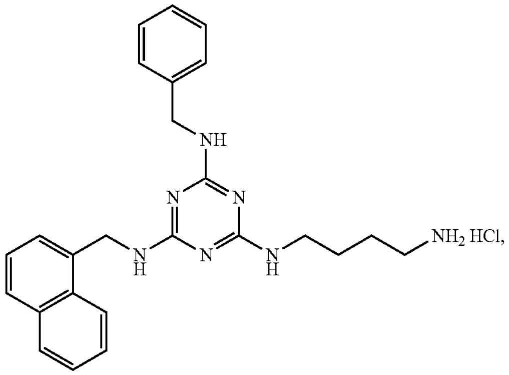
and
TN-5 HCl
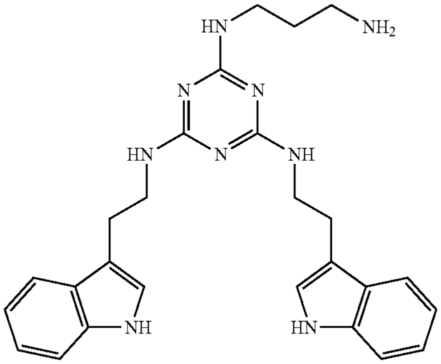
TZ-WKW
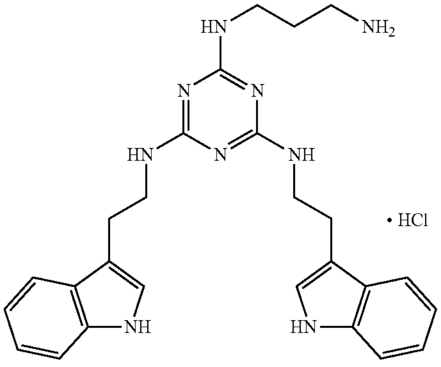
TZ-WKW HCl salt
-continued
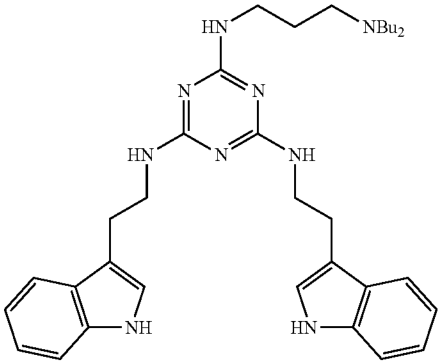
TZ-WK(Bu)2W
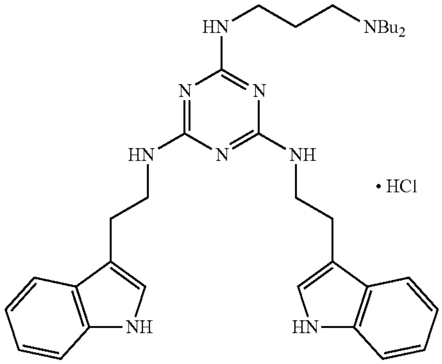
TZ-WK(Bu)2H HCl salt
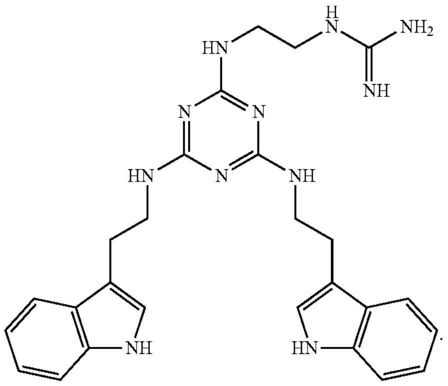
TZ-WRW
Preparation of Polymeric S-Triazines
Scheme 2
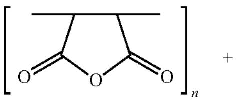

-continued

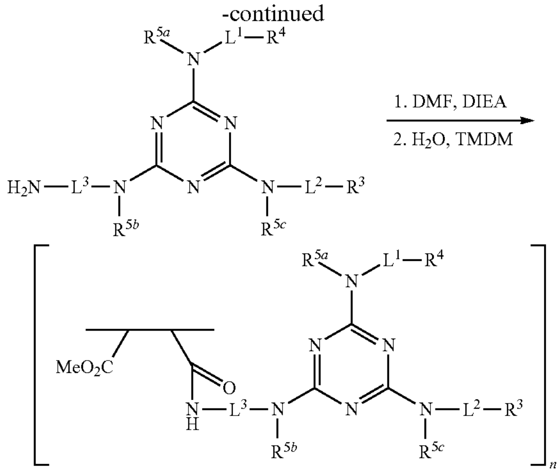

$L^1$, $L^2$, $L^3$, $R^1$, $R^4$, $R^{5a}$, $R^{5b}$, and $R^{5c}$ are as described herein.

The conjugation reaction between polymaleic anhydride (PMA) and 100 equivalent excess triazine compound of the invention is carried out overnight at 40° C. in DMF with agitation on a rotary shaker catalyzed by diisopropylethylamine (DIEA) (100 equiv). Unreacted maleic anhydride groups are then quenched by the addition of 150 μl distilled and deionized water, and the product treated with excess trimethylsilyldiazomethane (TMDM) to methylate the resulting carboxylic acid groups. After dialysis of the final solutions (5000 mwco, 1000 mL) against distilled water, polymeric products can be isolated (Scheme 2).

EXAMPLES

The following examples are presented in order to more fully illustrate the preferred embodiments of the invention. They should in no way be construed, however, as limiting the broad scope of the invention.

Biofilm Assays

Biofilms are sessile communities of cells that adhere to a variety of surfaces, including those of indwelling catheters and other medical devices (Nadell, 2009 #501). Pathogens such as *Pseudomonas, Staphyloccus* and *Acinetobacter* are all capable of biofilm formation. Due to their significantly enhanced tolerance to antibiotics, biofilms are implicated in many chronic infections associated with high morbidity and mortality (Hunter, 2008 #428). TN5 in particular prevents film formation.

Growth Inhibition Assays

The antimicrobial activity of each peptide can be tested following standard broth microdilution protocols recommended by the National Committee for Clinical Laboratory Standard. Multidrug-resistant *Staphylococcus aureus* strain (ATCC BAA-44) and *Acinetobacter baumannii* (ATCC BAA-747) can be used in this study, as well as Ampicillin- and streptomycin-resistant *Escherichia coli* (D31), obtained from the *E. coli* Genetic Resource Center (Yale University, New Haven, Conn.). Bacteria can be grown overnight in Tryptic Soy broth at 37° C. Then, cultures are diluted in Mueller-Hinton broth to a final concentration range of $2\times10^4$ to $2\times10^5$ CFU/ml. Bacterial inocula are incubated at 37° C. in phosphate-buffered saline (PBS) buffer (pH7.2) with various dilutions of peptide stock. The 18-hour absorbance data are used to calculate the percentage of inhibition for each sample by comparison with the absorbance of cultures without sample. Bacterial growth is measured by turbidity as optical density at 600 nm ($OD_{600}$), using a Genesys 5 Spectrophotometer (Rochester, N.Y.) or equivalent instrument. All assays can be carried out in triplicate. The concentration of peptide that results in 50% inhibition of growth is recorded as the $IC_{50}$. In addition the concentration of agents needed can be monitored to reduce the bacterial population by three logs, $IC_{99.9}$. This is a more rigorous indicator of the amount needed to prevent an infection.

Hemolytic Activity

Hemolytic activity of triazine compounds is assessed using fresh sheep erythrocytes (Fitzgerald Inc., Concord, Mass.). The red blood cell suspension is incubated in PBS buffer (pH 7.2) with varying concentrations of sample stocks at 37° C. for 30 minutes, and then spun down at 3,000 rpm for 10 mins. The resulting supernatant is diluted by a factor of 40 with distilled water. The absorbance of the supernatant at 540 nm is measured using a Genesys 5 Spectrophotometer. Zero % and 100% hemolysis controls are obtained by incubating the cells with buffer and 1% Triton-X, respectively.

Microplate-Based Assays of Biofilm Formation

This assay is based on the protocols described previously (Li, 2001 #745; Pratt, 1998 #725) with slight modifications. Briefly, *E. coli* RP437 or the test strain is used to form biofilms in 96 well plates in the presence of dendrimer peptides $(RW)_{4D}$ or other agents. An overnight culture of *E. coli* RP437 grown in LB medium is used to inoculate LB medium in 96 well plates to an $OD_{600}$ of 0.05. The peptides can be added to a final concentration of 0, 5, 10, 20, or 40 μM, respectively. Four replicates are tested for each condition. All samples are incubated at 37° C. without shaking for 24 hours to form the film. Then planktonic cells are removed and the plates with biofilms are washed three times with DI $H_2O$ and dried by gentle patting on a piece of paper towel. To stain the biofilms, 300 μL of 0.1% crystal violet is added into each well and incubated for 20 minutes at room temperature. Then the plates are washed three times with DI $H_2O$ to remove extra staining dye. $OD_{540}$ is then measured to quantify the biofilm on the bottom of each well.

Live/Dead Staining Assay of Biofilm Formation.

Polished stainless steel coupons (¼' long, ½' wide, and 1/16' thick) are used to form biofilms. An overnight culture of *E. coli* RP437 or the test strain grown in LB medium is used to inoculate a petri dish containing 20 mL LB medium and coupons to an $OD_{600}$ of 0.05 as measured by a Genesis 5 Spectrophotometer (Spectronic Instruments, Rochester, N.Y.). The coupons are initially polished using fine 3M Sand Blaster sandpapers (St. Paul, Minn.) and autoclaved for sterilization. To form biofilms, the stainless steel coupons are incubated in a plastic petri dish (60×15 mm) containing 6 mL LB medium supplemented with dendrimer peptides (0, 5, 10, 20, or 40 μM, respectively) at 37° C. without shaking for 24 hours. Two coupons will be tested for each condition. To analyze films using fluorescence microscopy, the biofilms are stained with Live/Dead BacLight™ bacterial viability kit (Cat# L7012, Invitrogen Corporation, California). Each coupon is washed by dipping vertically in 0.85% NaCl buffer three times (changing to fresh buffer after each dipping). Then they are soaked in 1 mL of 0.85% NaCl buffer containing 0.6 μL of 3.34 mM SYTO 9 and 2.4 μL of 20 mM propidium iodide in dark for 15 minutes. Images are recorded using an AXIO Imager M1 microscope (Carl Zeiss, Germany). Five spots on each coupon are randomly picked and analyzed.

Assay of Mature Biofilms.

*E. coli* RP437 or the test strain is used to form biofilms as described above, except that the peptides or mimetics are added to the existing biofilms at 24 hours after inoculation.

Duplicate coupons are tested for each condition. The coupons are washed as before and incubated in 0.85% NaCl buffer supplemented with dendrimer peptides or mimetic agents at concentrations of 0, 20, 40, 80, 120, or 160 μM at 37° C. without shaking for 3 hours. After treatment, all coupons are washed immediately with fresh 0.85% NaCl buffer and stained in 1 mL of 0.85% NaCl buffer containing 0.6 μL of 3.34 mM SYTO 9 and 2.4 μL of 20 mM propidium iodide in the dark for 15 minutes. Images are recorded as described above. Again five spots on each coupon are randomly picked for analysis.

Example 1

Antibacterial Testing

The antimicrobial activity of each triazine compound was tested by following standard broth microdilution protocols recommended by the National Committee for Clinical Laboratory Standard. All compounds were initially tested against *Bacillus subtilis* (ATCC 6633; Rockville, Md.). Bacteria were grown in Mueller Hinton Broth (MHB) at 37° C. for overnight. Then, cultures were diluted in MHB to a final concentration of $2\times10^4$ to $2\times10^5$ CFU/mL. Bacterial inocula were incubated at 37° C. in PBS buffer (pH 7.2) with varying concentrations of 2-fold dilution of triazine stocks. The 18-hour absorbance data were used to calculate the percent inhibition for each sample by comparing with the absorbance of cultures without triazine compounds. Bacterial growth was measured by turbidity as optical density at 600 nm using a Genesys 5 Spectrophotometer (Rochester, N.Y.). The concentration of peptide that resulted in 50% was recorded as $MIC_{50}$.

Example 2

Hemolytic Activity

Hemolytic activity of three triazine compounds Is assessed on fresh sheep erythrocytes (Fitzgerald Inc., Concord, Mass.). The red blood cell suspension Is incubated in PBS buffer (pH 7.2) with varying concentrations of sample stocks at 37° C. for 30 minutes, and then spun down at 3,000 rpm for 10 mins. The resulting supernatant is diluted by a factor of 40 in distilled water. The absorbance of the supernatant at 540 nm is measured using a Genesys 5 Spectrophotometer. Zero hemolysis and 100% hemolysis controls are obtained by incubating the cells with buffer and 1% Triton-X, respectively. Sample concentration yielding 50% hemolysis is used as hemolytic dose ($HD_{50}$) determined from dose-response curves.

Example 3

Calcein Dye Leakage

To test whether the active triazine compounds kill bacteria via disrupting membrane integrity, a calcein dye leakage experiment can be carried out with ampicillin and one of the triazine compounds with little antimicrobial activity (h-9) as control. The method of preparation of dye-encapsulated vesicles has been reported in detail. Lasch, V.; Weissig, M. *Brandl in Liposomes: a Practical Approach* Eds.: Taylor, K. M. G.; Craig, D. Q. M. Oxford University Press, Oxford, 2003; pp. 10-12. The fraction of leakage was calculated from the fluorescence intensity at 515 nm, with 100% leakage calibrated by addition of 1% Triton X-100.

Assays and Assay Results

The above s-triazines were tested against Gram positive and negative MDR organisms, including *A. Baumannii, E. coli* D31, and *Staphyloccus Aureus* (MRSA). The s-triazines showed potent antibacterial activity against planktonic cells of these species with encouraging HI values, especially relative to any natural AMP's. In addition TN-5 prevents formation of biofilms by *E. coli*. Furthermore, *A. baumannii* does not acquire resistance to TN-5 after exposure to 400 generations of sublethal concentrations of TN-5. This is in marked contrast to two antibiotics that are in clinical use today, gentamycin and vancomycin. These results are summarized in Tables 1-3 and FIGS. 1-4, below.

In particular, FIG. 1 depicts the results of the experimental evaluation of the ability of *A. baumannii* to evolve resistance to sublethal TN5 and the AMP indolicidin relative to two antibiotics in current use. Changes in the $IC_{50}$ of cultures exposed to sublethal doses of TN5 are expressed as ratios of the new to original values. For reference, the response of these cells to ciprofloxacin and gentamycin, two current antibiotics is shown. In the latter cases, there is a significant increase in the $IC_{50}$ on 400 generations of exposure.

The $IC_{50}$ value in each case was determined, and then the ratio of hemolytic activity (hemolytic index, HI) to the $IC_{50}$ was calculated, a number referred to herein as the HI value. Natural peptides tend to have very low HI values, which has restricted their utility as antimicrobials.

TABLE 1

Biological activity of the TN series of triazines

| Compound | Bacteria | $MIC_{50}$ (μg/mL) | $MIC_{90}$ (μg/mL) | $HD_{50}$ (μg/mL) | HI |
|---|---|---|---|---|---|
| TN1 | *A. baumannii* | 96 | 143 | 631.4 | 6.58 |
| | *E. coli* D31 | 112.5 | 192 | | 5.6 |
| | *S. aureus* | 62 | 94 | | 10.2 |
| TN2 | *A. baumannii* | 12.8 | 15.8 | 840.8 | 65.7 |
| | *E. coli* D31 | 26.9 | 55.6 | | 31.1 |
| | *S. aureus* | 12.1 | 14.55 | | 69.5 |
| TN3 | *A. baumannii* | 50.8 | 77.4 | 901.9 | 17.8 |
| | *E. coli* D31 | 40 | 84.8 | | 22.5 |
| | *S. aureus* | 50.1 | 71.3 | | 18 |
| TN4 | *A. baumannii* | 302.5 | 462.5 | 221.3 | 0.73 |
| | *E. coli* D31 | 18.8 | 62.5 | | 11.77 |
| | *S. aureus* | 68 | 117.5 | | 3.25 |
| TN5 | *A. baumannii* | 3 | 5.1 | 167.5 | 55.83 |
| | *E. coli* D31 | 4.75 | 8.9 | | 35.26 |
| | *S. aureus* | 5.9 | 9.8 | | 28.39 |

TABLE 2

Biological activity of the TZ series of compounds

| | *E. Coli* | | *S. Aureus* | | *B. Subtilis* | |
|---|---|---|---|---|---|---|
| Triazines | $MIC_{50}$ (ug/mL) | $MIC_{90}$ (ug/mL) | $MIC_{50}$ (ug/mL) | $MIC_{90}$ (ug/mL) | $MIC_{50}$ (ug/mL) | $MIC_{90}$ (ug/mL) |
| TZ-WKW | 4.5 | 6.0 | 3.4 | 4.4 | 1.5 | 2.3 |
| TZ-WK(Bu)$_2$W | 21.3 | 55.2 | 1.8 | 2.4 | 1.0 | 3.1 |
| TZ-WRW | 4.1 | 9.1 | 3.3 | 3.5 | 2.9 | 5.1 |
| TZ-(RW)$_3$ | 64.2 | 83.2 | 35.8 | 44.8 | 8.8 | 21.4 |
| Vancomycin | 191.8 | >200 | 0.8 | 1.2 | <0.8 | <0.8 |

TABLE 3

HI values for TZ compounds assayed in Table 2

| Triazines | *E. coli* $IC_{50}$ (ug/mL) | *E. coli* HI | *S. aureus* $IC_{50}$ (ug/mL) | *S. aureus* HI | *B. subtilis* $IC_{50}$ (ug/mL) | *B. subtilis* HI | $HD_{50}$ (ug/mL) |
|---|---|---|---|---|---|---|---|
| TZ-WKW | 4.5 | 14.1 | 3.4 | 19.1 | 1.5 | 43.3 | 65 |
| TZ-WK(Bu)$_2$W | 21.3 | 4.3 | 1.8 | 50.8 | 1.0 | 91.5 | 91.5 |
| TZ-WRW | 4.1 | 10.6 | 3.3 | 13.2 | 2.9 | 15 | 43.6 |

The Response of an *E. coli* Biofilm to TN-5

The strain for this experiment used was *E. coli* RP437/pRSH103, a strong film forming strain. The surface studied was that of a 96 well plate. Culture conditions were 24 hours or 48 hours of incubation in Luria-Bertani Broth (LB) supplemented with 10 m/mL tetracycline at 37° C. The following assays were performed:

1. Measurement of total cell growth in each well using $OD_{600}$.
2. Quantification of the biofilm at the bottom of each well by staining with 0.1% crystal violet and reading $OD_{540}$.
2. Quantification of total biofilm by dissolving the crystal violet with ethanol and reading at $OD_{540}$ Absorbance at 540 nm and 600 nm with the medium and triazine only (no cells) was also measured to control the results by subtracting the background reading.

Figure 3:
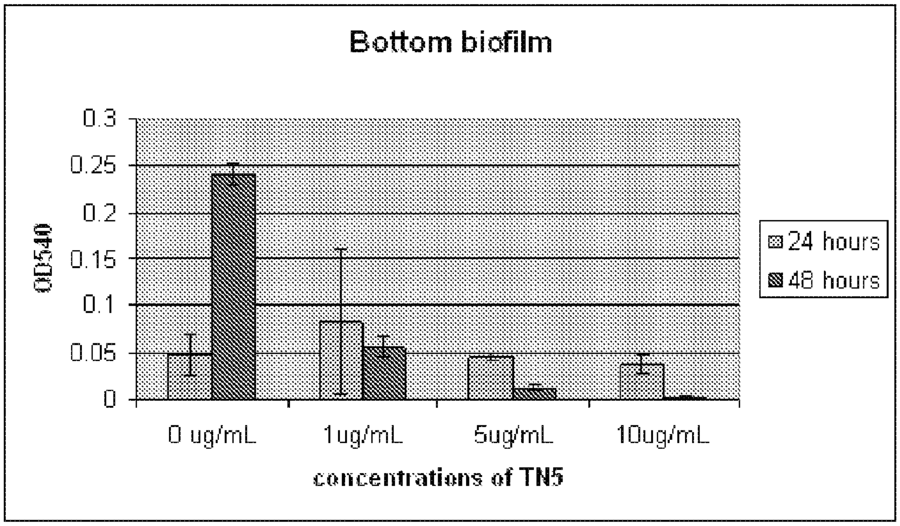
FIG. 3 shows the bottom biofilm measured at $OD_{540}$.
Figure 4:
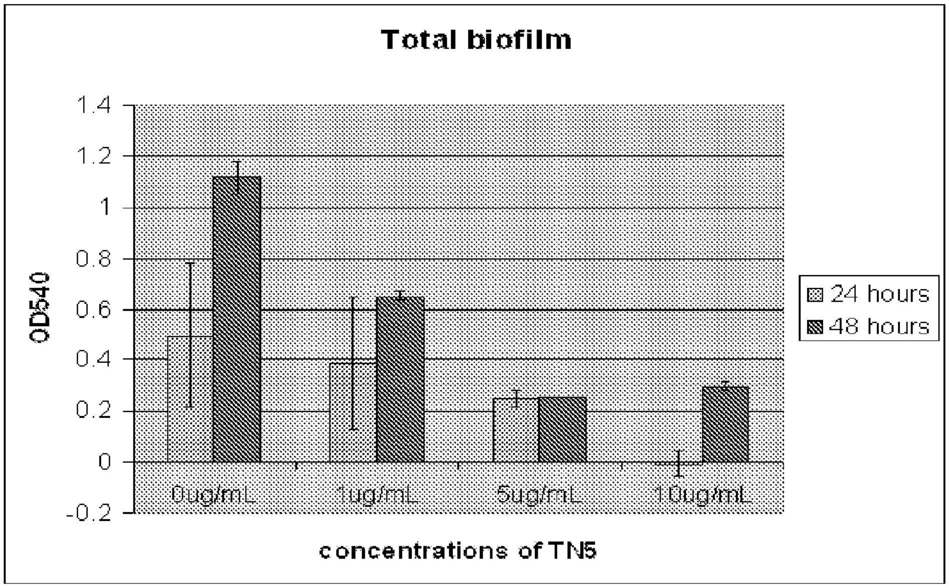
FIG. 4 shows the total biofilm measured at $OD_{540}$.

In the concentration range from 0-5 μg/mL, TN-5 does not inhibit growth of planktonic cells (FIG. 3). However, TN-5 inhibited biofilm formation at 1, 5, 10 μg/mL (FIGS. 4 to 5).

REFERENCES

1. Zasloff, M. 2002. Antimicrobial peptides of multicellular organisms. *Nature* 415(6870):389-95.
2. Boman, H. G. 2003. Antibacterial peptides: basic facts and emerging concepts. *J. Intern. Med.* 254(3):197-215.
3. Medzhitov, R. and C. Janeway, Jr. 2000. Innate immune recognition: mechanisms and pathways. *Immunol. Rev.* 173:89-97.
4. Brogden, K. A., Ackermann, M., McCray, P. B., and Tack, B. F. 2003. Antimicrobial peptides in animals and their role in host defences. *Int J Antimicrob Agents* 22(5):465-78.
5. Hancock, R. E. 1999. Host defence (cationic) peptides: what is their future clinical potential? *Drugs* 57(4):469-73.
6. Fischetti, V. A. 2003. Novel method to control pathogenic bacteria on human mucous membranes. *Ann. N. Y. Acad. Sci.* 987:207-14.
7. Yeaman, M. R. and Yount, N. Y. 2003. Mechanisms of antimicrobial peptide action and resistance. *Pharmacol Rev.* 55:27-55.
8. Strøm, M. B., Haug, B. E., Skar, M. L., Stensen, W., Stiberg, T. and Svendsen, J. S. 2003. The pharmocophore of short cationic antibacterial peptides. *J. Med. Chem.* 46(9):1567-1570.
9. Liu, Z., Brady, A., Young, A., Rasimick, B., Chen, K., Zhou, C. and Kallenbach, N. R. 2007. Length effects in antimicrobial peptides of the (RW)n Series. *Antimicrobial Agents and Chemotherapy* 51(2):597-603.
10. Arvidsson, P. I., Frackenpohl, J., Ryder, N. S., Leichty, B., Petersen, F., Zimmermann, H., Camenisch, G. P., Woessner, R. and Seebach, D. 2001. On the antimicrobial and hemolytic activities of amphiphilic β-peptides. *ChemBioChem* 2(10):771-773.

11. Goodson, B., Ehrhardt, A., Ng, S., Nuss, J., Johnson, K., Giedlin, M., Yamamoto, R., Moos, W. H., Krebber, A., Ladner, M., Giacona, M. B., Vitt, C. and Winter, J. 1999. Characterization of novel antimicrobial peptoids. *Antimicrobial Agents and Chemotherapy* 43(6):1429-1434.
12. Rennie, J., Arnt, L., Tang, H., Nuesslein, K. and Tew, G. N. 2005. Simple oligomers as antimicrobial peptide mimics. *J. Industrial Microbiology & Biotech.* 32(7):296-300.
13. Silen, J. L., Lu, A. T., Solas, D. W., Gore, M. A., Maclean, D., Shah, N. H., Coffin, J. M., Bhinderwala, N. S., Wang, Y., Tsutsui, K. T., Look, G. C., Campbell, D. A., Hale, R. L., Navre, M. and DeLuca-Flaherty, C. R. 1998. Screening for novel antimicrobials from encoded combinatorial libraries by using a two-dimensional agar format. *Antimicrobial Agents and Chemotherapy* 42(6):1447-1453.
14. Giacometti, A., Cirioni, O., Greganti, G., Quarta, M. and Scalise, G. 1998. In vitro activities of membrane-active peptides against gram-positive and gram-negative aerobic bacteria. *Antimicrobial Agents and Chemotherapy* 42(12):3320-3324.
15. Giacometti, A., Cirioni, O., Barchiesi, F., Del Prete, M. S, and Scalise, G. 1999. Antimicrobial activity of polycationic peptides. *Peptides* 20(11):1265-1273.
16. Huang, H. W. 2000. Action of antimicrobial peptides: two-state model. *Biochemistry* 39(29):8347-8352.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for nucleic acids or poly(s-triazine) compounds are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. A s-triazine compound having a formula:

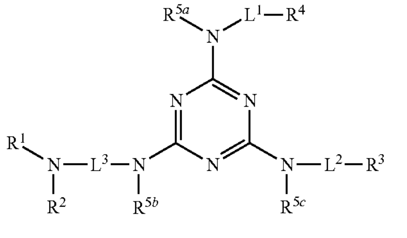

I wherein $L^1$ is a single bond, and $L^2$ is $C_1$-$C_4$ alkylene; or $L^1$ is $C_1$-$C_4$ alkylene, and $L^2$ is a single bond or $C_1$-$C_4$ alkylene;

$L^3$ is selected from $C_2$-$C_6$ alkylene, $C_2$-$C_6$ alkenyl, and $C_2$-$C_6$ alkynyl;

each of $R^1$ and $R^2$ is independently substituted or unsubstituted $C_1$-$C_6$ alkyl; or $R^1$ and $R^2$ may join together to form a 4-7 membered heterocycloalkyl; or $R^1$ is H; and $R^2$ is —C(=NH)—$NH_2$;

$R^3$ is $R^4$; or $R^3$ is selected from substituted or unsubstituted aryl and substituted or unsubstituted heteroaryl;

$R^4$ is substituted or unsubstituted

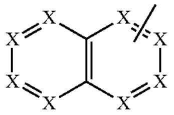

or

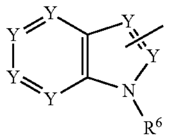

each X is C or N; provided that no more than three Xs are N at one time; and the X through which the $R^4$ is attached to $L^1$ or $L^2$ is C;

each Y is C or N; provided that no more than three Ys are N at one time; and the Y through which the $R^4$ is attached to $L^1$ or $L^2$ is C;

$R^6$ is H or substituted or unsubstituted $C_1$-$C_6$ alkyl;

each $R^{5a}$, $R^{5b}$, or $R^{5c}$ is independently H or substituted or unsubstituted $C_1$-$C_6$ alkyl;

or a pharmaceutically acceptable salt thereof;

or stereoisomers, or tautomers thereof.

2. The compound according to claim 1, wherein the compound is according to formula II:

II

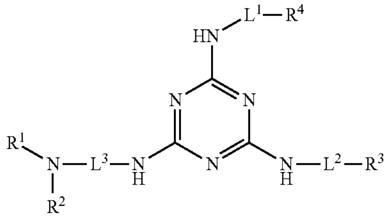

wherein $L^1$, $L^2$, $L^3$, $R^1$, $R^2$, $R^3$ and $R^4$ are as in claim 1;

or a pharmaceutically acceptable salt thereof;

or stereoisomers, or tautomers thereof.

3. The compound according to claim 1, wherein $R^4$ is substituted or unsubstituted

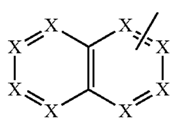

each X is C or N; provided that no more than three Xs are N at one time.

4. The compound according to claim 1, wherein $R^4$ is naphthalenyl, quinolinyl, isoquinolinyl, naphthyridinyl, quinazolinyl, quinoxalinyl, phthalazinyl, or cinnolinyl, unsubstituted or substituted with one or more alkyl, halo, haloalkyl, carboxy, amino, or cyano.

5. The compound according to claim 1, wherein $R^4$ is substituted or unsubstituted

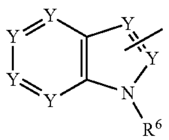

each Y is C or N; provided that no more than three Ys are N at one time;

$R^6$ is H or substituted or unsubstituted $C_1$-$C_6$ alkyl.

6. The compound according to claim 1, wherein $R^4$ is indolyl, imidazolyl, or pyridopyrrolidinyl, unsubstituted or substituted with one or more of alkyl, halo, haloalkyl, amino, carboxy, or cyano.

7. The compound according to claim 1, wherein the compound is according to formula IIIa or IIIb:

IIIa

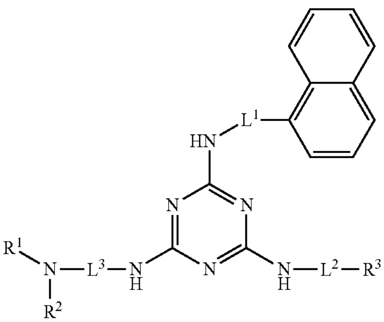

or

IIIb

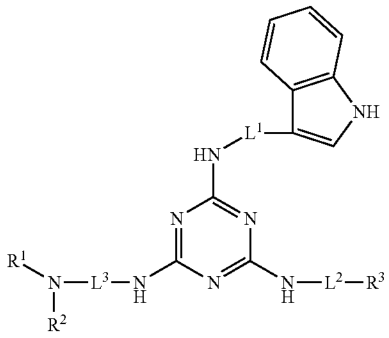

wherein $L^1$, $L^2$, $L^3$, $R^1$, $R^2$, and $R^3$ are as in claim 1;

or a pharmaceutically acceptable salt thereof;

or stereoisomers, or tautomers thereof.

8. The compound according to claim 1, wherein $L^1$ is a single bond, $—CH_2—$, or $CH_2—CH_2—$.

9. The compound according to claim 1, wherein the compound is according to formula IVa, IVb, IVc, or IVd:

IVa

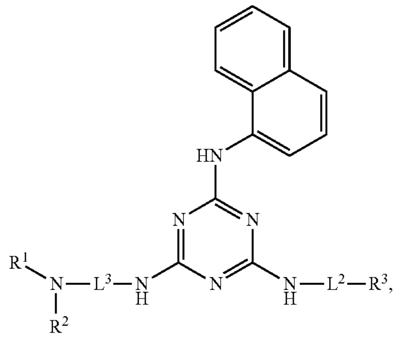

IVb

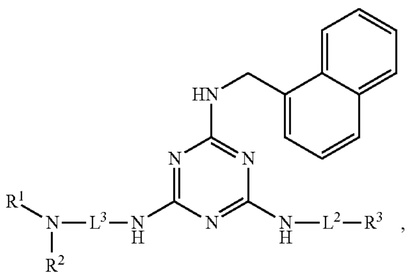

,

-continued

IVc

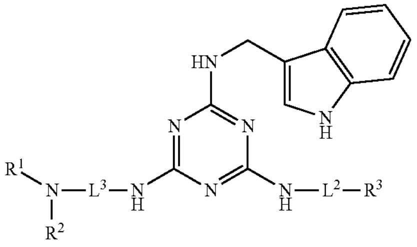

or

IVd

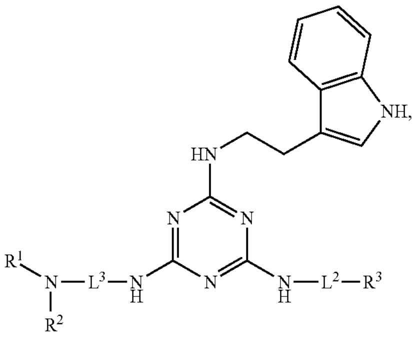

wherein $L^2$, $L^3$, $R^1$, $R^2$, and $R^3$ are as in claim 1;

or a pharmaceutically acceptable salt thereof;

or stereoisomers, or tautomers thereof.

10. The compound according to claim 1, wherein $R^3$ is phenyl, naphthyl, pyridyl, indolyl, or quinolinyl, unsubstituted or substituted with one or more substituents independently selected from halo, hydroxyl, amino, cyano, sulfo, sulfanyl, sulfinyl, amido, carboxy, ester, alkyl, substituted alkyl, alkenyl, substituted alkenyl, alkynyl, substituted alkynyl, and sulfonamide.

11. The compound according to claim 1, wherein the compound is according to formula Va, Vb, Vc, or Vd:

Va

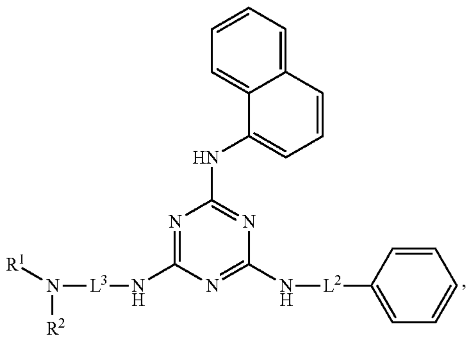

,

Vb

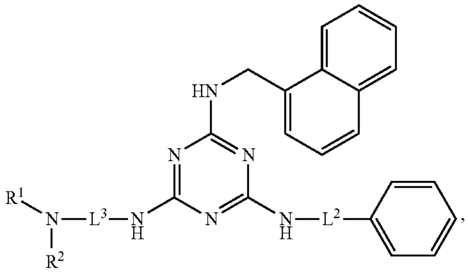

,

-continued

Vc

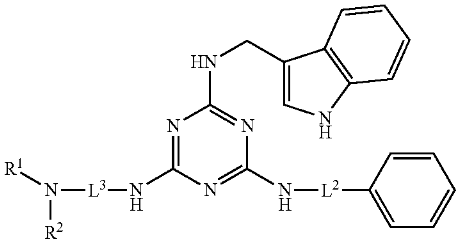

or

Vd

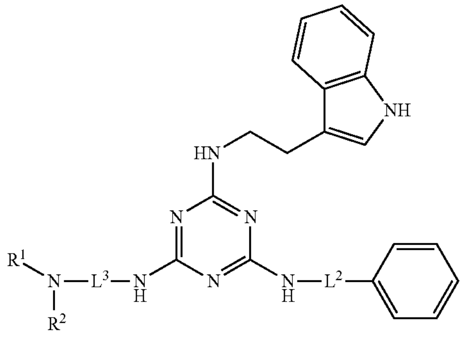

, wherein $L^2$, $L^3$, $R^1$, and $R^2$ are as in claim 1;

or a pharmaceutically acceptable salt thereof;

or stereoisomers, or tautomers thereof.

12. The compound according to claim 1, wherein the compound is according to formula VIa, VIb, VIc, or VId:

VIa

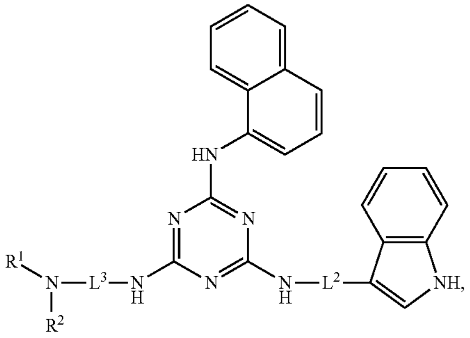

VIb

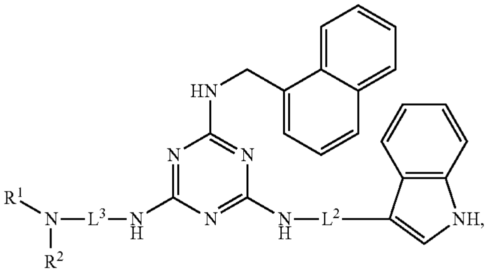

-continued

VIc

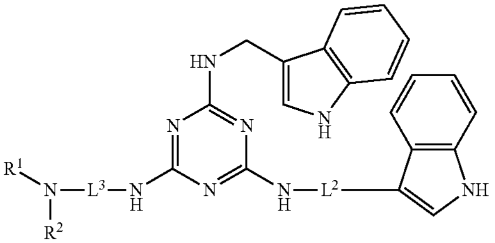

or

VId

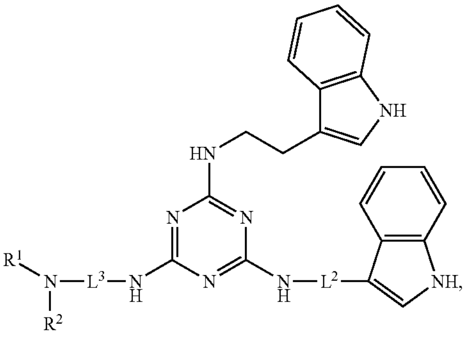

wherein $L^2$, $L^3$, $R^1$, and $R^2$ are as in claim 1;

or a pharmaceutically acceptable salt thereof;

or stereoisomers, or tautomers thereof.

13. The compound according to claim 1, wherein $L^1$ is a single bond, and $L^2$ is $-CH_2-$, $CH_2-CH_2-$ or $-CH_2-CH_2-CH_2-$; or $L^1$ is $-CH_2-$, $-CH_2-CH_2-$, or $-CH_2-CH_2-CH_2-$, and $L^2$ is a single bond, $-CH_2-$, $-CH_2-CH_2-$, or $-CH_2-CH_2-CH_2-$.

14. The compound according to claim 1, wherein the compound is according to formula VIIa, VIIb, VIIc, or VIId:

VIIa

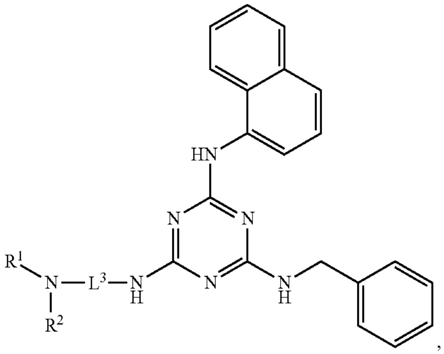

,

VIIb

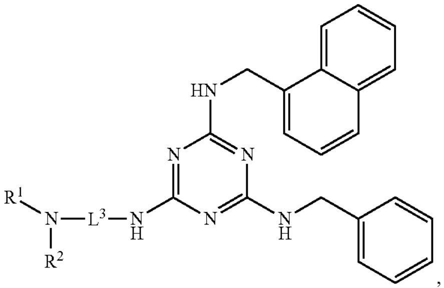

,

-continued

VIIc

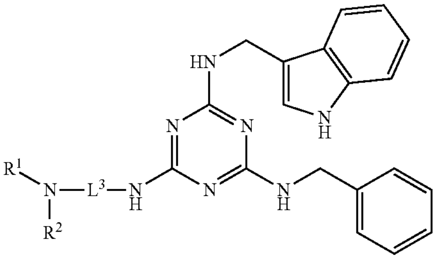

or

VIId

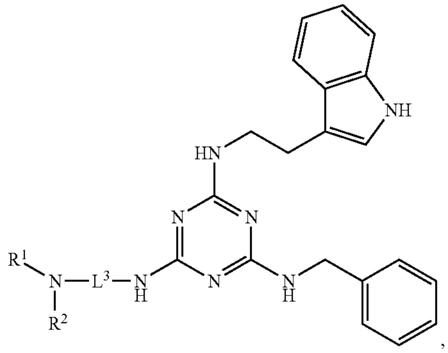

, wherein $L^3$, $R^1$, and $R^2$ are as in claim 1;

or a pharmaceutically acceptable salt thereof;

or stereoisomers, or tautomers thereof.

15. The compound according to claim 1, wherein the compound is according to formula VIII:

VIII

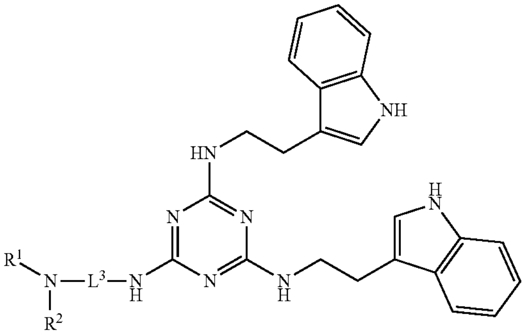

wherein $L^3$, $R^1$, and $R^2$ are as in claim 1;

or a pharmaceutically acceptable salt thereof;

or stereoisomers, or tautomers thereof.

16. The compound according to claim 1, wherein $L^3$ is $-CH_2-$, $-CH_2-CH_2-$, $-CH_2-CH_2-CH_2-$, or $-CH_2-CH_2-CH_2-CH_2-$.

17. The compound according to claim 1, wherein each $R^1$ and $R^2$ is independently unsubstituted $C_1$-$C_6$ alkyl; or $R^1$ is H; and $R^2$ is $-C(=NH)-NH_2$.

18. The compound according to claim 1, wherein the compound is according to formula IXb, or IXd:

IXa

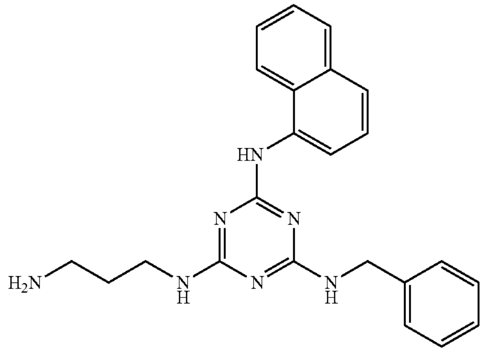

,

IXb

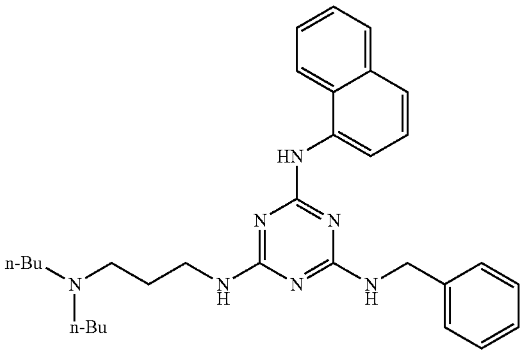

,

IXc

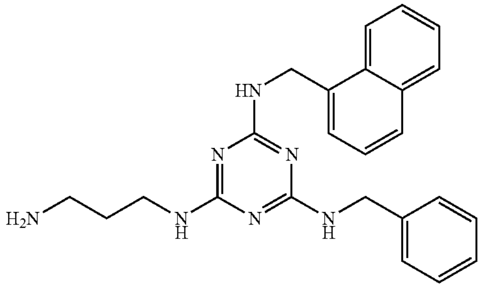

or

IXd

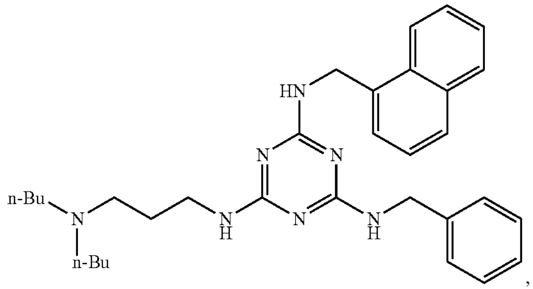

, or a pharmaceutically acceptable salt thereof;

or stereoisomers, or tautomers thereof.

19. The compound according to claim 1, wherein the compound is according to formula Xb, or Xc:

Xa

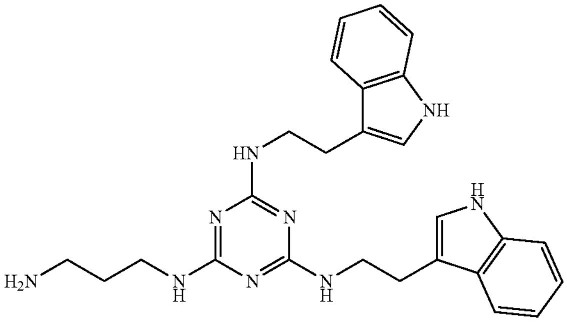

,

Xb

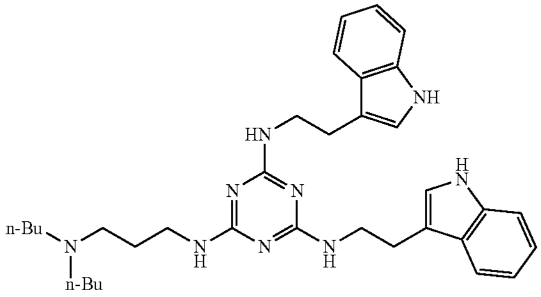

or

Xc

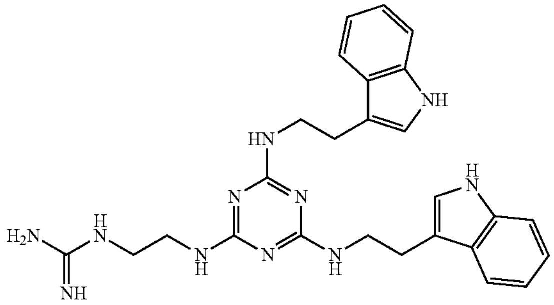

, or a pharmaceutically acceptable salt thereof;

or stereoisomers, or tautomers thereof.

20. The compound according to claim 1, wherein the compound is a pharmaceutically acceptable salt.

21. A pharmaceutical composition comprising a pharmaceutically acceptable carrier and a pharmaceutically effective amount of a compound of claim 1.

22. The pharmaceutical composition of claim 21, wherein the carrier is a parenteral, oral or topical carrier.

23. A method for treating a bacterial infection which comprises administering to a patient in need of such treatment, a therapeutically effective amount of the pharmaceutical composition of claim 21; wherein the bacterial infection is due to *A. Baumannii, E. coli* D31, or *Staphyloccus* Aureus (MRSA).

24. A pharmaceutically acceptable salt of a compound according to formula IXa, or TN-3:

IXa
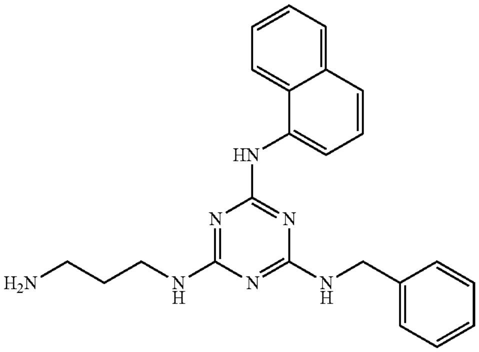
or
TN-3
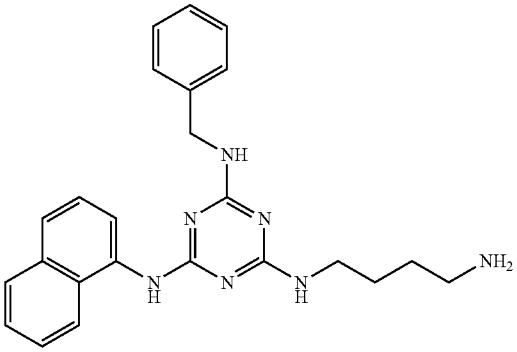
or a stereoisomer, or a tautomer thereof.
25. A pharmaceutically acceptable salt of a compound according to formula IXc, Xa, or TN-5:
IXc
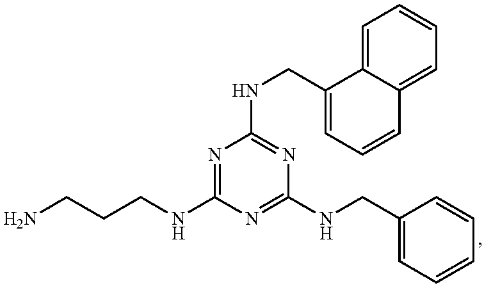
-continued
Xa
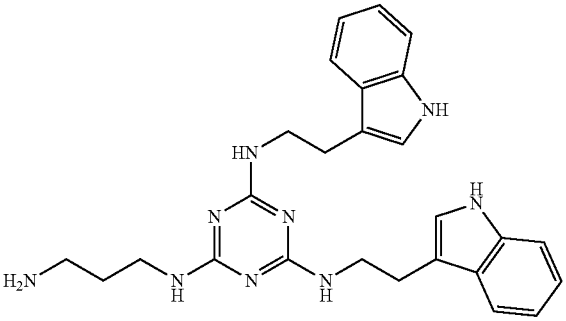
or
TN-5
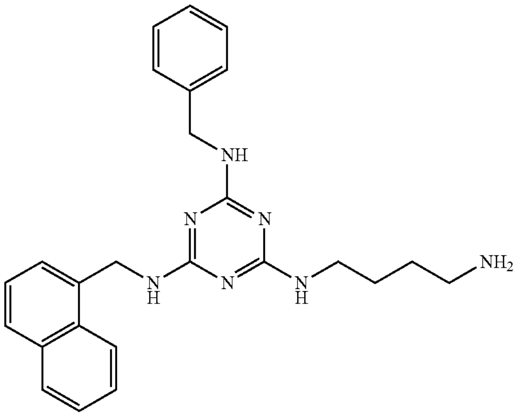
or a stereoisomer, or a tautomer thereof.
* * * * *